(12) United States Patent
Gurnett et al.

(10) Patent No.: US 7,718,390 B2
(45) Date of Patent: May 18, 2010

(54) TOXOPLASMA GONDII CYLCLIC GMP DEPENDENT PROTEIN KINASE G AS A CHEMOTHERAPEUTIC TARGET FOR ANTIPROTOZOAL AGENTS

(75) Inventors: Anne Gurnett, New York, NY (US); Robert Donald, South Orange, NJ (US); Georgianna Harris, Tinton Falls, NJ (US); Paul A. Liberator, Holmdel, NJ (US); Dennis Schmatz, Cranford, NJ (US); Sandra J. Rattray, Somerset, NJ (US)

(73) Assignee: Merial Limited, Duluth, GA (US)

( * ) Notice: Subject to any disclaimer, the term of this patent is extended or adjusted under 35 U.S.C. 154(b) by 332 days.

(21) Appl. No.: 11/525,062

(22) Filed: Sep. 21, 2006

(65) Prior Publication Data

US 2007/0009979 A1    Jan. 11, 2007

Related U.S. Application Data

(62) Division of application No. 10/348,155, filed on Jan. 21, 2003, now Pat. No. 7,125,700, which is a division of application No. 09/521,511, filed on Mar. 8, 2000, now Pat. No. 6,555,358.

(60) Provisional application No. 60/129,058, filed on Apr. 13, 1999.

(51) Int. Cl.
*C12Q 1/48* (2006.01)
*C12N 9/12* (2006.01)

(52) U.S. Cl. .......................................... 435/15; 435/194

(58) Field of Classification Search ........................ None
See application file for complete search history.

(56) References Cited

U.S. PATENT DOCUMENTS 6,555,358 B1 * 4/2003 Gurnett et al. ............ 435/258.4
7,125,700 B2 * 10/2006 Gurnett et al. .............. 435/194

OTHER PUBLICATIONS

Branden et al., "Introduction to Protein Structure", Garland Publishing Inc., New York, 1999, p. 247.*
Witkowski et al., Biochemistry 38:11643-11650, 1999.*
Feil et al., "High-level expression of functional cGMP-dependent protein kinase using the baculovirus system", FEBS Lett. 336:163-167, 1993.*
GenBank Accession No. P00516, "CGMP-Dependent Protein Kinase, Alpha Isozyme", Nov. 1997.*
Ann KS et al., "Protein Substrates for cGMP-Dependent Protein Phosphorylation in Cilia of Wild Type and *atalanta* Mutants of *Paramecium*", Cell Motility and the Cytoskeleton 30:252-260 (1995).
Walczak CE et al., "In vitro phosphorylation of ciliary dyneins by protein kinases from *Paramecium*", Journal of Cell Science 106, 1369-1376 (1993).
Kawwamoto F et al., "The roles of Ca2+/calmodulin- and cGMP-dependent pathways in gametogenesis of a rodent malaria parasite, *Plasmodium berghei*.", Eur J Cell Biol. Feb. 1993;60(1):101-7.
Miglietta Lap et al., "A Novel cGMP-dependent Protein Kinase from *Paramecium*", JBC vol. 263, No. 31, Issue of Nov. 5, pp. 1609 & 16105, 1988.
Donald R et al., "Molecular characterization of a coccidian parasite cGMP dependent protein kinase", Molecular & Biochemical Parasitology 120 (2002) 165-175.
Shiao et al., A comparison of various methods for the determination of viability of parasitic flagellates. Southeast Asian Journal of Tropical Medicine and Public Health. Dec. 1987, vol. 18, No. 4, pp. 539-546, see entire document.

* cited by examiner

*Primary Examiner*—David J Steadman
(74) *Attorney, Agent, or Firm*—Judy Jarecki-Black; Merial Limited; Thomas Kowalski, Esq.

(57) ABSTRACT

Protozoal cyclic GMP dependent protein kinases have been isolated and cloned. These enzymes may be used in screening assays to identify potential antiprotozoal agents.

4 Claims, No Drawings

SEQUENCE LISTING

<160> NUMBER OF SEQ ID NOS: 16

<210> SEQ ID NO 1
<211> LENGTH: 8
<212> TYPE: PRT
<213> ORGANISM: Artificial Sequence
<220> FEATURE:
<223> OTHER INFORMATION: Inhibitor Binding Protein

<400> SEQUENCE: 1

Ala Glu Asn Arg Gln Phe Leu Ala
 1               5

<210> SEQ ID NO 2
<211> LENGTH: 5
<212> TYPE: PRT
<213> ORGANISM: Artificial Sequence
<220> FEATURE:
<223> OTHER INFORMATION: Inhibitor Binding Protein

<400> SEQUENCE: 2

Val Leu Tyr Ile Leu
 1               5

<210> SEQ ID NO 3
<211> LENGTH: 5
<212> TYPE: PRT
<213> ORGANISM: Artificial Sequence
<220> FEATURE:
<223> OTHER INFORMATION: Inhibitor Binding Protein

<400> SEQUENCE: 3

Leu Val Ser Ile Lys
 1               5

<210> SEQ ID NO 4
<211> LENGTH: 16
<212> TYPE: PRT
<213> ORGANISM: Artificial Sequence
<220> FEATURE:
<223> OTHER INFORMATION: Inhibitor Binding Protein

<400> SEQUENCE: 4

Glu Asp Thr Gln Ala Glu Asp Ala Arg Leu Leu Gly His Leu Glu Lys
 1               5                  10                  15

```
<210> SEQ ID NO 5
<211> LENGTH: 19
<212> TYPE: PRT
<213> ORGANISM: Artificial Sequence
<220> FEATURE:
<223> OTHER INFORMATION: Inhibitor Binding Protein

<400> SEQUENCE: 5

Glu Met Pro Thr Ala Ser Thr Gly Thr Pro Glu Gln Gln Gln Gln Gln
 1               5                  10                  15

Gln Gln Gln

<210> SEQ ID NO 6
<211> LENGTH: 17
<212> TYPE: PRT
<213> ORGANISM: Artificial Sequence
<220> FEATURE:
<223> OTHER INFORMATION: Inhibitor Binding Protein

<400> SEQUENCE: 6

His Gly Glu Glu Gln Gln Gln Glu Arg Lys Pro Ser Gln Gln Gln Gln
 1               5                  10                  15

Asn

<210> SEQ ID NO 7
<211> LENGTH: 6
<212> TYPE: PRT
<213> ORGANISM: Artificial Sequence
<220> FEATURE:
<223> OTHER INFORMATION: Inhibitor Binding Protein
<220> FEATURE:
<221> NAME/KEY: VARIANT
<222> LOCATION: (4)...(4)
<223> OTHER INFORMATION: Xaa = Any Amino Acid

<400> SEQUENCE: 7

Val Phe Leu Xaa Ile Val
 1               5

<210> SEQ ID NO 8
<211> LENGTH: 453
<212> TYPE: DNA
<213> ORGANISM: Artificial Sequence
<220> FEATURE:
<223> OTHER INFORMATION: Probe

<400> SEQUENCE: 8
gaggataccc aggcggagga cgcgagacta ctgggtcacc tggagaagcg ggagaaaact     60
ccttcggact tgtctttaat tcgggattct ctttcaacta atttagtttg ttcttcttta    120
aatgacgcgg aagtggaggc tttggccaac gcggtggagt tcttcacttt caaaaaggga    180
gacgttgtca ccaaacaggg cgagagcggc agttatttct tcattgttca gcgggggag     240 tttgaggtga ttgtgaacga caaagtggtg aacaagattc taacgggcca ggcctttggg    300
gaaatttctt taattcataa ttctgcaaga actgcaacaa tcaaaaccct cagcgaagat    360
gcagccttgt ggggcgtcca gagacaagtc ttcagggaaa ccctaaagca gctgagcagc    420
agaaactttg ccgagaaccg ccagttcctt gca                                 453

<210> SEQ ID NO 9
<211> LENGTH: 151
<212> TYPE: PRT
<213> ORGANISM: Artificial Sequence
```

<220> FEATURE:
<223> OTHER INFORMATION: PKG

<400> SEQUENCE: 9

```
Glu Asp Thr Gln Ala Glu Asp Ala Arg Leu Leu Gly His Leu Glu Lys
 1               5                  10                  15
Arg Glu Lys Thr Pro Ser Asp Leu Ser Leu Ile Arg Asp Ser Leu Ser
            20                  25                  30
Thr Asn Leu Val Cys Ser Ser Leu Asn Asp Ala Glu Val Glu Ala Leu
        35                  40                  45
Ala Asn Ala Val Glu Phe Phe Thr Phe Lys Lys Gly Asp Val Val Thr
    50                  55                  60
Lys Gln Gly Glu Ser Gly Ser Tyr Phe Phe Ile Val His Ser Gly Glu
65                  70                  75                  80
Phe Glu Val Ile Val Asn Asp Lys Val Val Asn Lys Ile Leu Thr Gly
                85                  90                  95
Gln Ala Phe Gly Glu Ile Ser Leu Ile His Asn Ser Ala Arg Thr Ala
            100                 105                 110
Thr Ile Lys Thr Leu Ser Glu Asp Ala Ala Leu Trp Gly Val Gln Arg
        115                 120                 125
Gln Val Phe Arg Glu Thr Leu Lys Gln Leu Ser Ser Arg Asn Phe Ala
    130                 135                 140
Glu Asn Arg Gln Phe Leu Ala
145                 150
```

<210> SEQ ID NO 10
<211> LENGTH: 4262
<212> TYPE: DNA
<213> ORGANISM: Artificial Sequence
<220> FEATURE:
<223> OTHER INFORMATION: PKG

<400> SEQUENCE: 10

```
ccagaggctg acgggtggtt attgcttctc cgtttgagtc ccgcgcgcac ccttggatcg     60
tgctgtcttt cctttgcgct gcagcagcgc cgcgtgttac ggcagcagca gcagcagcag    120
cagcacaccc aacaacagca ggaatttgac gcttaattta gcgtggcacc ccagcagcag    180
gagcagcagc agtctagggc ttcactgacg tgcgcgttca cagcagcagc agcagcagct    240
gcagcagcgg caacagcaac agtagtagta gcggcagcag cagctgcaga gcagcagcg     300
gcagcagcgt cagagtcagt tgctgcctct tcctctctag ctgctgccca caatatgaat    360
gggatcagca gcagcaacag caacagtagc agcagcagca gcagcagcag tgacagcccg    420
ccgtcggcag ttaatcattt gtagcatctc aagccacggg agcagcagca gcgcagcaac    480
agcagcagga gctccattcc ttgtatgggt gtggggaggc attctggtgg ccctctagc     540
tgctgctgca gcagcagcag cagcagcagc agcaacacgc gctgccttgc cgatcgcagc    600
agtttacact gaaatgggc gcatgcagct ctaaggcgca gcaccagacc cgagatccgg     660
agccacgaga gcagcaggct gcgcaagaac agaaatcaac aggcccgagc ggcgctccta    720
acgacgcccc cgcacctgct gaggcggaga ggaagatgtc ggggtcaagc gccacagctc    780
ccaagggcga aatgcccacg gccagtacgg gcaccccgga gcagcaacag cagcaacagc    840
agcagcagca gcagcagcag gaacagcagc agcaccccga gcatcagcag tcagagaagc    900
agcagcagca tggggaggag cagcagcaag agaggaaacc ctcgcagcag cagcaaaatg    960
aagaagcagc agcaccccac aagcacggtg gagagcggaa ggtccagaag gcaattaagc   1020
```

-continued

```
agcaggaaga cactcaagca gaagatgcga gactactggg tcacctggag aagcgggaga    1080
aaactccttc ggacttgtct ttaattcggg attctctttc aactaattta gtttgttctt    1140
ctttaaatga cgcggaagtg gaggctttgg ccaacgcggt ggagttcttc actttcaaaa    1200
agggagacgt tgtcaccaaa cagggcgaga gcggcagtta tttcttcatt gttcacagcg    1260
gggagtttga ggtgattgtg aacgacaaag tggtgaacaa gattctaacg ggccaggcct    1320
ttggggaaat ttctttaatt cataattctg caagaactgc aacaatcaaa accctcagcg    1380
aagatgcagc cttgtggggc gtccagagac aagtcttcag ggaaacccta aagcagctga    1440
gcagcagaaa ctttgccgag aaccgacagt tcttggcttc tgtgaaattc tttgaaatgt    1500
tgacggaggc ccagaagaat gtgataacca acgcgctggt ggtgcagtct ttccagcccg    1560
gccaggcaat tgttaaggaa ggagaaaaag agatgttct ttacatttta aaagtggca    1620
aagccctcgt gtccatcaaa aacaagaag tccgggttct ccagcgggga aatactttg    1680
gcgagcgggc gctgctttat gatgaacctc gaagtgcaac aataacagca gaagagccga    1740
cagtttgtgt ctccattggc agagacctt tggacagggt tttggggaat ctgcagcacg    1800
tgctcttccg caatattatg ctcgaggcac tgcagcagag caaggtcttc gcctcttcc    1860
cgacggagca gctgagccgc ttaattggct ctgtagtggt taaggactat cccgaaaatt    1920
atatttttt ggatcgagaa aaccgcacaa gggcgtcggc gtcggcgctg ttctcggcgc    1980
aaggcgtgcg tttcttcttc gtgttggagg agagggttc tgtgtttgcc tacaaagaca    2040
agtccagcag cagcagcagc agcagcagca gcagcagcag cagcagcagc gcggagggg    2100
aaatggagct gcacctcata gatacctaa aaaggggaca agcttttgga gacgaatatg    2160
ttttgtctcc caacaaaccc tttgcgcatt gcgtcaagag caacgggccg acgaagctcg    2220
cgctgctgac ggctagcgcg ctgaccgcca cttttggggg acaagacatt gacgaaaccc    2280
tcgactataa caacaaatta gcgatcacga aaaagatgta tattttagg tatttgtcgg    2340
agcagcaaac gcaaacccta atcaaggcct tcaagaccgt cagatacact caggggaat    2400
ccatcattcg ggaaggcgaa atagggtctc ggttcttcat catcaagctt ggagaagtgg    2460
tgattctgaa gggcgaaaag cgggtgcgca cgctgggccg tcacgactac ttcggcgaga    2520
gggctttgct gcacgacgag cggcggtctg caacagtagc agcaaacagt cccgaggtgg    2580
atctgtgggt tgtcgacaaa gatgttttcc tccaaatcgt caagggccc atgcttaccc    2640
acttggagga gcgcattcgc atgcaagaca ccaaagttga attcaaagac ttgaatgttg    2700
tccgagtggt cggcagaggg acgttcggga ctgtaaagct ggtgcagcac attcccacgc    2760
aaatgcgcta cgccttaaaa tgcgtttcga gaaaagtgt tgtggcttta aatcaacaag    2820
accacattcg actagaaaga gagataatgg cagaaaacga ccaccccttc atcattcgcc    2880
tggtgcggac attccgggat aaggagtttc tgtatttctt gacggagctg gtgacgggtg    2940
gagagctgta cgacgctatt cggaagttgg gtcttttagg gaggtaccag gcgcagtttt    3000
acttggcctc gatcgtgctg gccatcgagt acctgcacga gcggaacatc gcgtaccggg    3060
acttgaagcc ggagaacatt ttgctggatt ctcagggata cgtcaaactc atcgacttcg    3120
gctgcgccaa aaaaatgcag ggaagagcct acacgctcgt gggaactccg cactacatgg    3180
cgccggaggt cattttggga aaaggatata ctctaacagc agacacttgg gcctttgggg    3240
tttgtcttta cgaattcatg tgcggccctt tgccctttgg aaacgacgcg gaggaccagc    3300
tcgagatctt cagagacatt ctcgcaggca aactcatatt ccccccactac gtgactgacc    3360
aagacgccat aaaaccttatg aagcggctgc tgtgccgttt gcctgaagtg cggattggct    3420
```

-continued

```
gctcaattaa tggatacaaa gacattaagg agcacgcctt cttctcggac ttcgactggg    3480
acagacttgc agggagagat ttgtctcctc cgcttttgcc taagggagaa atctacgcag    3540
aagacgcgga ggagggagga ttggatattg aggaagacga gggcatagaa cttgaagacg    3600
aatatgaatg ggacaaggac ttctaaaccc taaaccctag caaaccctaa accctcgttt    3660
tggtgcttta gcctcttcgg ctttttctcc ctaaccgatt taccaagctg ccattgtgca    3720
gcagcagtga gggtcttcgc aatattttcg tttggaaatt tgctgctgct gctgcagcag    3780
cagcagcagc ggcagtggcg gcagcagcag cggcagccca ctctgtgcga cgagagctgt    3840
tgctgctgtg ggtgcgctgc tgctctcgct gctgccgttg cagcaccgca gcagcagcag    3900
cagcagcagc ggcagcagca gcagcggcag cagcagcagc agcgtgtctg actgttttg     3960
ctgctattct gtaatcatat tttgttggtt ctttagtgtt tgcaccttaa actcttgccg    4020
ttggctttgc tgctgcagtg ctgctgcagc ggcggtttgc tgatgctgct gcagcggcgg    4080
tttgctgatg ctgctgcagc ggcggtttgc tgctgctgct gctgctgctg cagcgcgaag    4140
ccagacttga gcccgcgtag ggtctttccg attgctgcag ctgtcgacgc agagtctctt    4200
tattgtttta tataaattat taaacaaaaa taaaaaaata aaataaaaa aaaaaaaaaa     4260
aa                                                                  4262
```

<210> SEQ ID NO 11
<211> LENGTH: 1003
<212> TYPE: PRT
<213> ORGANISM: Artificial Sequence
<220> FEATURE:
<223> OTHER INFORMATION: PKG

<400> SEQUENCE: 11

```
Met Gly Ala Cys Ser Ser Lys Ala Gln His Gln Thr Arg Asp Pro Glu
  1               5                  10                  15

Pro Arg Glu Gln Gln Ala Ala Gln Gln Lys Ser Thr Gly Pro Ser
             20                  25                  30

Gly Ala Pro Asn Asp Ala Pro Ala Pro Ala Glu Ala Glu Arg Lys Met
         35                  40                  45

Ser Gly Ser Ser Ala Thr Ala Pro Lys Gly Glu Met Pro Thr Ala Ser
     50                  55                  60

Thr Gly Thr Pro Glu Gln Gln Gln Gln Gln Gln Gln Gln Gln Gln Gln
 65                  70                  75                  80

Gln Gln Glu Gln Gln Gln His Pro Glu His Gln Ser Glu Lys Gln
                 85                  90                  95

Gln Gln His Gly Glu Glu Gln Gln Glu Arg Lys Pro Ser Gln Gln
            100                 105                 110

Gln Gln Asn Glu Glu Ala Ala Ala Pro His Lys His Gly Gly Glu Arg
        115                 120                 125

Lys Val Gln Lys Ala Ile Lys Gln Gln Glu Asp Thr Gln Ala Glu Asp
    130                 135                 140

Ala Arg Leu Leu Gly His Leu Glu Lys Arg Glu Lys Thr Pro Ser Asp
145                 150                 155                 160

Leu Ser Leu Ile Arg Asp Ser Leu Ser Thr Asn Leu Val Cys Ser Ser
                165                 170                 175

Leu Asn Asp Ala Glu Val Glu Ala Leu Ala Asn Ala Val Glu Phe Phe
            180                 185                 190

Thr Phe Lys Lys Gly Asp Val Val Thr Lys Gln Gly Glu Ser Gly Ser
        195                 200                 205
```

-continued

```
Tyr Phe Phe Ile Val His Ser Gly Glu Phe Glu Val Ile Val Asn Asp
    210                 215                 220

Lys Val Val Asn Lys Ile Leu Thr Gly Gln Ala Phe Gly Glu Ile Ser
225                 230                 235                 240

Leu Ile His Asn Ser Ala Arg Thr Ala Thr Ile Lys Thr Leu Ser Glu
                245                 250                 255

Asp Ala Ala Leu Trp Gly Val Gln Arg Gln Val Phe Arg Glu Thr Leu
            260                 265                 270

Lys Gln Leu Ser Ser Arg Asn Phe Ala Glu Asn Arg Gln Phe Leu Ala
        275                 280                 285

Ser Val Lys Phe Phe Glu Met Leu Thr Glu Ala Gln Lys Asn Val Ile
    290                 295                 300

Thr Asn Ala Leu Val Val Gln Ser Phe Gln Pro Gly Gln Ala Ile Val
305                 310                 315                 320

Lys Glu Gly Glu Lys Gly Asp Val Leu Tyr Ile Leu Lys Ser Gly Lys
                325                 330                 335

Ala Leu Val Ser Ile Lys Asn Lys Glu Val Arg Val Leu Gln Arg Gly
            340                 345                 350

Glu Tyr Phe Gly Glu Arg Ala Leu Leu Tyr Asp Glu Pro Arg Ser Ala
        355                 360                 365

Thr Ile Thr Ala Glu Glu Pro Thr Val Cys Val Ser Ile Gly Arg Asp
    370                 375                 380

Leu Leu Asp Arg Val Leu Gly Asn Leu Gln His Val Leu Phe Arg Asn
385                 390                 395                 400

Ile Met Leu Glu Ala Leu Gln Gln Ser Lys Val Phe Ala Ser Phe Pro
                405                 410                 415

Thr Glu Gln Leu Ser Arg Leu Ile Gly Ser Val Val Lys Asp Tyr
            420                 425                 430

Pro Glu Asn Tyr Ile Ile Leu Asp Arg Glu Asn Arg Thr Arg Ala Ser
        435                 440                 445

Ala Ser Ala Leu Phe Ser Ala Gln Gly Val Arg Phe Phe Val Leu
    450                 455                 460

Glu Gly Glu Val Ser Val Phe Ala Tyr Lys Asp Lys Ser Ser Ser Ser
465                 470                 475                 480

Ser Ser Ser Ser Ser Ser Ser Ser Ser Ala Glu Gly Glu
                485                 490                 495

Met Glu Leu His Leu Ile Asp Thr Leu Lys Arg Gly Gln Ala Phe Gly
            500                 505                 510

Asp Glu Tyr Val Leu Ser Pro Asn Lys Pro Phe Ala His Cys Val Lys
        515                 520                 525

Ser Asn Gly Pro Thr Lys Leu Ala Leu Leu Thr Ala Ser Ala Leu Thr
    530                 535                 540

Ala Thr Leu Gly Gly Gln Asp Ile Asp Glu Thr Leu Asp Tyr Asn Asn
545                 550                 555                 560

Lys Leu Ala Ile Thr Lys Lys Met Tyr Ile Phe Arg Tyr Leu Ser Glu
                565                 570                 575

Gln Gln Thr Gln Thr Leu Ile Lys Ala Phe Lys Thr Val Arg Tyr Thr
            580                 585                 590

Gln Gly Glu Ser Ile Ile Arg Glu Gly Glu Ile Gly Ser Arg Phe Phe
        595                 600                 605

Ile Ile Lys Leu Gly Glu Val Val Ile Leu Lys Gly Glu Lys Arg Val
    610                 615                 620
```

-continued

Arg Thr Leu Gly Arg His Asp Tyr Phe Gly Glu Arg Ala Leu Leu His
625                 630                 635                 640

Asp Glu Arg Arg Ser Ala Thr Val Ala Ala Asn Ser Pro Glu Val Asp
            645                 650                 655

Leu Trp Val Val Asp Lys Asp Val Phe Leu Gln Ile Val Lys Gly Pro
        660                 665                 670

Met Leu Thr His Leu Glu Glu Arg Ile Arg Met Gln Asp Thr Lys Val
    675                 680                 685

Glu Phe Lys Asp Leu Asn Val Val Arg Val Val Gly Arg Gly Thr Phe
690                 695                 700

Gly Thr Val Lys Leu Val Gln His Ile Pro Thr Gln Met Arg Tyr Ala
705                 710                 715                 720

Leu Lys Cys Val Ser Arg Lys Ser Val Val Ala Leu Asn Gln Gln Asp
                725                 730                 735

His Ile Arg Leu Glu Arg Glu Ile Met Ala Glu Asn Asp His Pro Phe
            740                 745                 750

Ile Ile Arg Leu Val Arg Thr Phe Arg Asp Lys Glu Phe Leu Tyr Phe
        755                 760                 765

Leu Thr Glu Leu Val Thr Gly Gly Glu Leu Tyr Asp Ala Ile Arg Lys
    770                 775                 780

Leu Gly Leu Leu Gly Arg Tyr Gln Ala Gln Phe Tyr Leu Ala Ser Ile
785                 790                 795                 800

Val Leu Ala Ile Glu Tyr Leu His Glu Arg Asn Ile Ala Tyr Arg Asp
                805                 810                 815

Leu Lys Pro Glu Asn Ile Leu Leu Asp Ser Gln Gly Tyr Val Lys Leu
            820                 825                 830

Ile Asp Phe Gly Cys Ala Lys Lys Met Gln Gly Arg Ala Tyr Thr Leu
        835                 840                 845

Val Gly Thr Pro His Tyr Met Ala Pro Glu Val Ile Leu Gly Lys Gly
    850                 855                 860

Tyr Thr Leu Thr Ala Asp Thr Trp Ala Phe Gly Val Cys Leu Tyr Glu
865                 870                 875                 880

Phe Met Cys Gly Pro Leu Pro Phe Gly Asn Asp Ala Glu Asp Gln Leu
                885                 890                 895

Glu Ile Phe Arg Asp Ile Leu Ala Gly Lys Leu Ile Phe Pro His Tyr
            900                 905                 910

Val Thr Asp Gln Asp Ala Ile Asn Leu Met Lys Arg Leu Leu Cys Arg
        915                 920                 925

Leu Pro Glu Val Arg Ile Gly Cys Ser Ile Asn Gly Tyr Lys Asp Ile
    930                 935                 940

Lys Glu His Ala Phe Phe Ser Asp Phe Asp Trp Asp Arg Leu Ala Gly
945                 950                 955                 960

Arg Asp Leu Ser Pro Pro Leu Leu Pro Lys Gly Glu Ile Tyr Ala Glu
                965                 970                 975

Asp Ala Glu Glu Gly Gly Leu Asp Ile Glu Glu Asp Glu Gly Ile Glu
            980                 985                 990

Leu Glu Asp Glu Tyr Glu Trp Asp Lys Asp Phe
            995                 1000

<210> SEQ ID NO 12
<211> LENGTH: 7796
<212> TYPE: DNA
<213> ORGANISM: Artificial Sequence
<220> FEATURE:
<223> OTHER INFORMATION: PKG -continued

<400> SEQUENCE: 12

```
cgagatcgcc caagacaggg acgagtttct cccgttcagc agagcggaga gctctagcgg      60
gttctgtccc tgctcaaaga gggcaagtcg tctcgcctct aacgcttgaa cgcagcgcgt     120
ctgggcgact ctccgagcga ctgctcccgt ttgcgaactt gcgtcgcgca gacccgctga     180
gaggctcgct gacgagggca gtcttttctac cacgttttcg tgtgctttca agagtgccgt     240
ctgtggtcga cagaaagatg gtgcaaaagc acgcaaagt tctcacggca gacaccagct     300
gcggtaatcg ctctcaaccg acacaggctc gtcgtttccg gctgtacagg cgccattagc     360
gagagttggc tgtgtccgag cagcaaaggc cgacatgtcc ttttctcgct tctccccgtt     420
cttttcccc tttccgtgct tcctgtattc aaaagagcga agagggcaa gaaaaggggg     480
aaaggcacga aggacataag tcgatcaaca gaaataatc cctccctgga ctcgctgctg     540
gtcccgcgcc agctagttgt cttttattag ggagggacct gagcgacgac cagggcgcgg     600
tcgccgtctc acgttctgcg cttcctgtcg gaatcgtttg ccagcgtttc agcggcagag     660
tgcaagacgc gaaggacagc cttagcaaac ggtcgcaaag cactccaccg tttccgccct     720
cgcggtgtct aaacactgcc gtctacgctg gtgaggtggc aaaggcggga gcgccacaga     780
tttgtgacgg cagatgcgac cctgcttttct tcttccttcg tcttctttct gctccgcaca     840
cctcgccact ggacgaaaga agaaggaagc agaagaaaga cgaggcgtgt ggagcggtga     900
ttgccgtctc ttcgcgcttc ttttcctctg cctcaggctc cttgtctgca aacggcagag     960
aagcgcgaag aaaaggagac ggagtccgag gaacagacgt cgagcacaca ccttttcttt    1020
cgtgtcgctt ccccggcttt cgtttctccc gctcgtgtgt ggaaaagaaa gcacagcgaa    1080
ggggccgaaa gcaaagaggg tcgcactcgt cccctctctc tctctctgct ccgtgttgca    1140
cttggcggct agcgtgagca ggggagagag agagagacga ggcacaacgt gaaccgccga    1200
tcggcgctcg actctcgtct ctccccgtct gctgcgctca cgtggcacct agccgcgagc    1260
tgagagcaga gaggggcaga cgacgcgagt gcaccgtgga cgcgcgctct ctgactggga    1320
actgacgggc gcgagccagc agcgactgcc gcgcgcgaga gactgaccct tgactgcccg    1380
cgctcggtcg tcgctgacgg acaagcctct cggcttctag gcgagaggac accgcgtacc    1440
agcggtcctc tgttcggaga gccgaagatc cgctctcctg tggcgcatgg tcgccaggag    1500
gttgtctctc ctcgcgcgaa aatgggcgct tgcatttcca aaaatagttc caacagagag    1560
gagcgcgctt ttacccgcga acgtaaaggt tttatcaag ggctcgcgtt tcacggtctt    1620
ctgctctgtc cgcctcgaaa caaacagttg ccgagcgcaa agtgccagaa gacgagacag    1680
gcggagcttt gtttgtcaac cggccagtgc accgccagga gcggcaggcg acgagacctc    1740
tgcgacgggt gccggtcacg tggcggtcct cgccgtccgc tgctctggag acgctgccca    1800
gctgccgaag aagcttcgag gaactcccctt gccagggtag acggaacgcg cgacggcttc    1860
ttcgaagctc cttgagggaa cggtcccatc tgccttgcgc agcctccgca gcggagttgg    1920
agagagctcc ggacggtgtg tgcccagacc tcggaggcg cgcctcaacc tctctcgagg    1980
cctgccacac acgggtctgg gcgaggaacc ggggacggcg aacgccgagc aaggaggcgt    2040
gacgagaag cgctccttgg cccctgccgc ttgcggctcg ttcctccgca ctgcctcttc    2100
aaagacacta gagagacact ggcagggatg aactctccca agactctgga tttctgtgat    2160
ctctctgtga ccgtccctac ttgagagggt tctgagacct ggcggaggcg caagaggacg    2220
accccaagcg cgaagcgccg aaccaggacg ccgcctccgc gttctcctgc tggggttcgc    2280
```

```
gcttcgcggc ttggtcctgc ttccctctga ggctccagaa ggcccgaaag aaaaacccgg    2340
cggagaccgg aagggagact ccgaggtctt ccgggctttc tttttgggcc gcctctggcc    2400
aaaccggcgc agaaggcgat tctgaagcaa gatgactcgc acacggagga tttggccgcg    2460
tcttccgcta agacttcgtt ctactgagcg tgtgcctcct agagaaactc aacgcgcacc    2520
tggcatatcg cgagaagacg cctgcagact tctctttgag ttgcgcgtgg accgtatagc    2580
gctcttctgc ggacgtctga ttgcgctgat ccaagacagc ctgaaggcga atcttgtctg    2640
ctcctctctg aacgcgacta ggttctgtcg gacttccgct tagaacagac gaggagagac    2700
aatgagggca aaatcgacgc tctcgcagtc gcgatgcagt tcttcacctt ttactcccgc    2760
tttagctgcg agagcgtcag cgctacgtca agaagtggaa caagaaaggc gacgtggtga    2820
ccaagcaggg cgaacctgga agctactttt gttctttccg ctgcaccact ggttcgtccc    2880
gcttggacct tcgatgaaaa tcatcattca cagcgggacg tttgacgtgc tcgtcaacga    2940
caagcgcgtt agtagtaagt gtcgccctgc aaactcacg agcagttgct gttcgcgcaa    3000
aatgcgatgg acaagggaaa agcctttgga gaaatcgcgc tcattcacaa ttacgctacc    3060
tgttcccttt tcggaaacct ctttagcgcg agtaagtgtt taccgaaaga tctgcgacgg    3120
ttgtcgcaag ctccacagaa ggtgccctct atggctttct agacgctgcc aacagcgttc    3180
gaggtgtctt ccacgggaga ggggtgtcca gcgtcacact tcagagaaa cgctgaagca    3240 gctgagcagc ccccacaggt cgcagtgtga aagtctcttt gcgacttcgt cgactcgtcg    3300
cgaaactttg cggagaacag acagttttg gcctccgtca agttcttcga ctttgaaac    3360 gcctcttgtc tgtcaaaaac cggaggcagt tcaagaagct aatgttgaca gaggcgcaga    3420
aaaacgtcat caccaatgcg ctggtcgtgg ttacaactgt ctccgcgtct ttttgcagta    3480
gtggttacgc gaccagcacc agaacttcaa gcctggacag cccattgtga aggaaggcga    3540
cgcaggagac tcttgaagtt cggacctgtc gggtaacact tccttccgct gcgtcctctg    3600
gtcctctaca tcttgaagag cggcaaagcg aaggtctcca tcggcggacg caggagatgt    3660
agaacttctc gccgtttcgc ttccagaggt agccgcctgc ggagatccgc atgctgcgga    3720
aaggcgacta cttcggagag cgcgcgttgc cctctaggcg tacgacgcct ttccgctgat    3780
gaagcctctc gcgcgcaacg tgtacaaaga gccgaggagc gcaaccatca cggcagaaga    3840
gttcaccgtc acatgtttct cggctcctcg cgttggtagt gccgtcttct caagtggcag    3900
tgcgtgtcga tcggccgcga gctgctggat cgcgtcttgg gaaatctgca acgcacagct    3960
agccggcgct cgacgaccta gcgcagaacc ctttagacgt gcacgttctg ttcagaaaca    4020
tcatggtcga ggctctgcag caaagcaaag cgtgcaagac aagtctttgt agtaccagct    4080
ccgagacgtc gtttcgtttc tctacgaatt gtttcaaggc gaccagctga gcaaattgat    4140
cgaagcggcc agatgcttaa caaagttccg ctggtcgact cgtttaacta gcttcgccgg    4200
gtggtgaagg actacggcgc agactacgtc attctggata aggaaaacaa caccacttcc    4260
tgatgccgcg tctgatgcag taagacctat cctttttgtt gacgaaggga attcgcttct    4320
tctttgtcct cgaaggagag ctgtcggtgt ctgcttccct taagcgaaga agaaacagga    4380
gcttcctctc gacagccaca acgcctacac acaaaaccca gcgacgaaag aggaagaacg    4440
gaagctcgca tgcggatgtg tgttttgggt cgctgctttc tccttcttgc cttcgagcgt    4500
gcgactctga aacgcggcca agcattcggt gaagaatacg tccttaatcc cgctgagact    4560
ttgcgccggt tcgtaagcca cttcttatgc aggaattagg cactcgacct ttcaaccact    4620
atgtcaaaag tgtcggccct tgcaagctcg gtgagctgga aagttggtga tacagttttc    4680
```

```
acagccggga acgttcgagc ctctgtttac ttcgtccgtg ttgacggcga ctttgggagg   4740
cgaagacatc gagacaaatg aagcaggcac aactgccgct gaaaccctcc gcttctgtag   4800
gatgagacgc tggacttcaa taacaaacgc gcgattattc ggaagatgta ctactctgcg   4860
acctgaagtt attgtttgcg cgctaataag ccttctacat cattttcaga tatctgtcag   4920
atcaccaaat gacgatgctc atcaaagctt gtaaaagtct atagacagtc tagtggttta   4980
ctgctacgag tagtttcgaa tcaaaactgt cagatacatg tcgggagagt acatcatcaa   5040
agaaggcgaa agtttgaca gtctatgtac agccctctca tgtagtagtt tcttccgctt    5100
cgcggcacac ggttcttcat catcaaagcc ggtgaagttg cgattctgaa gcgccgtgtg   5160
ccaagaagta gtagtttcgg ccacttcaac gctaagactt gaacaacaag cgcctccgca   5220
ccctcggccg ccacgactat tttggggaac cttgttgttc gcggaggcgt gggagccggc   5280
ggtgctgata aaacccttg gggcgttgct gtacgataag cctaggacgg cctctgtgtg    5340
tgccaattct cccgcaacga catgctattc ggatcctgcc ggagacacac acggttaaga   5400 gcggggtcg acctctgggt cgtcgataag tcggttttca acgaaatcat cgcccccagc    5460
tggagaccca gcagctattc agccaaaagt tgctttagta caaggggcct atgcttgctc   5520
acttggagga aagaatccgc atgcaagaca gttccccgga tacgaacgag tgaacctcct   5580
ttcttaggcg tacgttctgt ccaaggtcga gttccaggac ttgcaagtgg tcagagtggt   5640
cggcagagga ggttccagct caaggtcctg aacgttcacc agtctcacca gccgtctcct   5700
accttcggca ccgttaagct cgtgcgccat gtgccgacac atattcgcta tggaagccgt   5760
ggcaattcga gcacgcggta cacggctgtc tataagcgat gcgctcaag tgtgtctcaa    5820 ggcgaagcgt catcgctctc agtcagcaac acgcgagttc acacagagtt ccgcttcgca   5880
gtagcgagag tcagtcgttg aacacattcg cctggaacgc gaaatcatgg cggaaaacga   5940
ccatcctttc ttgtgtaagc ggaccttgcg ctttagtacc gccttttgct ggtaggaaag   6000
atcattcggc tagtgagaac gttccgcgac aaggagttcc tatacttcct tagtaagccg   6060
atcactcttg caaggcgctg ttcctcaagg atatgaagga cacggaactc gtcacaggag   6120
gcgaactgta cgatgccatc cggaagctag gtgccttgag cagtgtcctc cgcttgacat   6180
gctacggtag gccttcgatc gactgcttgc tcggtcgcag gcccagttct acctcgcctc   6240
cattgtcctc ctgacgaacg agccagcgtc cgggtcaaga tggagcggag gtaacaggag   6300
gccatcgagt atctccacga acgaaacatc gcgtacaggg acttgaagcc cggtagctca   6360
tagaggtgct tgctttgtag cgcatgtccc tgaacttcgg tgagaacatt ctcctcgaca   6420
gccaaggcta cgtcaaactc atcgatttcg actcttgtaa gaggagctgt cggttccgat   6480
gcagtttgag tagctaaagc gctgtgcgaa aaagatgcaa ggtcgcgcct acacccttgt   6540
cggcacacct cgacacgctt tttctacgtt ccagcgcgga tgtgggaaca gccgtgtgga   6600
cactacatgg ctcctgaagt cattcttggc aaggggtaca cgctgacggc gtgatgtacc   6660
gaggacttca gtaagaaccg ttccccatgt gcgactgccg agacacttgg gcgttcggcg   6720
tctgcctgta cgagttcatg tgcggacctc tctgtgaacc cgcaagccgc agacggacat   6780
gctcaagtac acgcctggag tcccttcgg aaacgatgct gaagatcaac tggaaatctt    6840
ccgagacatt aggggaagcc tttgctacga cttctagttg acctttagaa ggctctgtaa   6900
ctcacaggaa aactcgtttt cccgcactat gtcaccgacc aagatgcgat gagtgtcctt   6960
ttgagcaaaa gggcgtgata cagtggctgg ttctacgcta caacctgatg aagaggcttt   7020
```

-continued

```
tgtgtcgtct ccctgaggtc cgaatcggat gttggactac ttctccgaaa acacagcaga    7080
gggactccag gcttagccta gctccatcaa cggctacaag acatcaagg agcacgcatt     7140 tttcggagac cgaggtagtt gccgatgttc ctgtagttcc tcgtgcgtaa aaagcctctg    7200
ttcgactggg acaaactggc aggtcgtggc ttgccgccac ccctcgcacc aagctgaccc    7260
tgtttgaccg tccagcaccg aacggcggtg gggagcgtgg gaaaggcgaa acctacgcag    7320
aagatactga acaatcctct ttcgagctgg ctttccgctt tggatgcgtc ttctatgact    7380
tgttaggaga agctcgacc acgaggatga cacgatcgtt ttggaagacg agtatgactg     7440
ggacaaggat tgctcctact gtgctagcaa aaccttctgc tcatactgac cctgttccta    7500
ttctgatttt tcagcttagg tgtttgttcc ccgtcagtgc tgaaagtgcc aagactaaaa    7560
agtcgaatcc acaaacaagg ggcagtcacg actttcacgg gctccttctc tcttctgact    7620
cttctgtgga cctgcaactt cctgcatgac cgaggaagag agaagactga aagacacct     7680 ggacgttgaa ggacgtactg gaaacgatcc gtgcataagc atgagcgcga aaaaaaaaa     7740 aaaaaaaact tgctaggca cgtattcgta ctcgcgcttt tttttttttt tttttt         7796
```

<210> SEQ ID NO 13
<211> LENGTH: 994
<212> TYPE: PRT
<213> ORGANISM: Artificial Sequence
<220> FEATURE:
<223> OTHER INFORMATION: PKG

<400> SEQUENCE: 13

```
Met Gly Ala Cys Ile Ser Lys Asn Ser Ser Ala Arg Val Ser Arg Ser
 1               5                  10                  15

Ser Ala Leu Ser Ala Ser Lys Gln Thr Val Ala Ala Ser Ala Pro Pro
            20                  25                  30

Gly Ala Ala Gly Asp Glu Thr Ser Ala Thr Gly Ala Ala Glu Glu Ala
        35                  40                  45

Ser Arg Asn Ser Leu Ala Arg Val Asp Gly Thr Arg Ala Ser Ala Ala
    50                  55                  60

Glu Leu Glu Arg Ala Pro Asp Gly Val Cys Pro Asp Arg Glu Glu Pro
65                  70                  75                  80

Gly Thr Ala Asn Ala Glu Gln Gly Gly Val Thr Glu Lys Lys Asp Thr
                85                  90                  95

Arg Glu Thr Leu Ala Gly Met Asn Ser Pro Lys Thr Leu Glu Ala Glu
            100                 105                 110

Ala Gln Glu Asp Asp Leu Lys Arg Glu Ala Pro Asn Gln Asp Val Pro
        115                 120                 125

Ser Glu Ala Pro Glu Gly Pro Lys Glu Pro Gly Gly Asp Arg Lys
    130                 135                 140

Pro Ala Gln Lys Ala Ile Leu Lys Gln Asp Asp Ser His Thr Glu Glu
145                 150                 155                 160

Glu Lys Leu Asn Ala His Leu Ala Tyr Arg Glu Lys Thr Pro Ala Asp
                165                 170                 175

Phe Ala Leu Ile Gln Asp Ser Leu Lys Ala Asn Leu Val Cys Ser Ser
            180                 185                 190

Leu Asn Glu Gly Glu Ile Asp Ala Leu Ala Val Ala Met Gln Phe Phe
        195                 200                 205

Thr Phe Lys Lys Gly Asp Val Val Thr Lys Gln Gly Glu Pro Gly Ser
    210                 215                 220

Tyr Phe Phe Ile Ile His Ser Gly Thr Phe Asp Val Leu Val Asn Asp
```

-continued

```
                225                 230                 235                 240
Lys Arg Val Asn Ala Met Asp Lys Gly Lys Ala Phe Gly Glu Ile Ala
                    245                 250                 255
Leu Ile His Asn Thr Glu Arg Ser Ala Thr Val Val Ala Ser Ser Thr
                260                 265                 270
Glu Gly Ala Leu Trp Gly Val Gln Arg His Thr Phe Arg Glu Thr Leu
            275                 280                 285
Lys Gln Leu Ser Ser Arg Asn Phe Ala Glu Asn Arg Gln Phe Leu Ala
        290                 295                 300
Ser Val Lys Phe Phe Glu Met Leu Thr Glu Ala Gln Lys Asn Val Ile
305                 310                 315                 320
Thr Asn Ala Leu Val Val Glu Asn Phe Lys Pro Gly Gln Pro Ile Val
                    325                 330                 335
Lys Glu Gly Asp Ala Gly Asp Val Leu Tyr Ile Leu Lys Ser Gly Lys
                340                 345                 350
Ala Lys Val Ser Ile Gly Gly Arg Glu Ile Arg Met Leu Arg Lys Gly
            355                 360                 365
Asp Tyr Phe Gly Glu Arg Ala Leu Leu Tyr Lys Glu Pro Arg Ser Ala
        370                 375                 380
Thr Ile Thr Ala Glu Glu Phe Thr Val Cys Val Ser Ile Gly Arg Glu
385                 390                 395                 400
Leu Leu Asp Arg Val Leu Gly Asn Leu Gln His Val Leu Phe Arg Asn
                    405                 410                 415
Ile Met Val Glu Ala Leu Gln Gln Ser Lys Val Tyr Glu Leu Phe Gln
                420                 425                 430
Gly Asp Gln Leu Ser Lys Leu Ile Glu Ala Ala Val Val Lys Asp Tyr
            435                 440                 445
Gly Ala Asp Tyr Val Ile Leu Asp Lys Glu Asn Lys Thr Lys Gly Ile
        450                 455                 460
Arg Phe Phe Phe Val Leu Glu Gly Glu Leu Ser Val Tyr Ala Tyr Thr
465                 470                 475                 480
Gln Asn Pro Ala Thr Lys Glu Glu Arg Lys Leu Ala Ala Thr Leu
                    485                 490                 495
Lys Arg Gly Gln Ala Phe Gly Glu Glu Tyr Val Leu Asn Pro Thr Arg
            500                 505                 510
Pro Phe Asn His Tyr Val Lys Ser Val Gly Pro Cys Lys Leu Ala Leu
        515                 520                 525
Phe Thr Ser Ser Val Leu Thr Ala Thr Leu Gly Gly Glu Asp Ile Asp
        530                 535                 540
Glu Thr Leu Asp Phe Asn Asn Lys Arg Ala Ile Ile Arg Lys Met Tyr
545                 550                 555                 560
Ile Phe Arg Tyr Leu Ser Asp His Gln Met Thr Met Leu Ile Lys Ala
                    565                 570                 575
Phe Lys Thr Val Arg Tyr Met Ser Gly Glu Tyr Ile Ile Lys Glu Gly
                580                 585                 590
Glu Arg Gly Thr Arg Phe Phe Ile Ile Lys Ala Gly Glu Val Ala Ile
            595                 600                 605
Leu Lys Asn Asn Lys Arg Leu Arg Thr Leu Gly Arg His Asp Tyr Phe
        610                 615                 620
Gly Glu Arg Ala Leu Leu Tyr Asp Glu Pro Arg Thr Ala Ser Val Cys
625                 630                 635                 640
Ala Asn Ser Ala Gly Val Asp Leu Trp Val Val Asp Lys Ser Val Phe
                    645                 650                 655
```

-continued

Asn Glu Ile Ile Lys Gly Pro Met Leu Ala His Leu Glu Glu Arg Ile
            660                 665                 670

Arg Met Gln Asp Thr Lys Val Glu Phe Gln Asp Leu Gln Val Val Arg
        675                 680                 685

Val Val Gly Arg Gly Thr Phe Gly Thr Val Lys Leu Val Arg His Val
    690                 695                 700

Pro Thr Asp Ile Arg Tyr Ala Leu Lys Cys Val Ser Arg Arg Ser Val
705                 710                 715                 720

Ile Ala Leu Ser Gln Gln Gln His Ile Arg Leu Glu Arg Glu Ile Met
                725                 730                 735

Ala Glu Asn Asp His Pro Phe Ile Ile Arg Leu Val Arg Thr Phe Arg
            740                 745                 750

Asp Lys Glu Phe Leu Tyr Phe Leu Thr Glu Leu Val Thr Gly Gly Glu
        755                 760                 765

Leu Tyr Asp Ala Ile Arg Lys Leu Gly Leu Leu Ala Arg Ser Gln Ala
    770                 775                 780

Gln Phe Tyr Leu Ala Ser Ile Val Leu Ala Ile Glu Tyr Leu His Glu
785                 790                 795                 800

Arg Asn Ile Ala Tyr Arg Asp Leu Lys Pro Glu Asn Ile Leu Leu Asp
                805                 810                 815

Ser Gln Gly Tyr Val Lys Leu Ile Asp Phe Gly Cys Ala Lys Lys Met
            820                 825                 830

Gln Gly Arg Ala Tyr Thr Leu Val Gly Thr Pro His Tyr Met Ala Pro
        835                 840                 845

Glu Val Ile Leu Gly Lys Gly Tyr Thr Leu Thr Ala Asp Thr Trp Ala
    850                 855                 860

Phe Gly Val Cys Leu Tyr Glu Phe Met Cys Gly Pro Leu Pro Phe Gly
865                 870                 875                 880

Asn Asp Ala Glu Asp Gln Leu Glu Ile Phe Arg Asp Ile Leu Thr Gly
                885                 890                 895

Lys Leu Val Phe Pro His Tyr Val Thr Asp Gln Asp Ala Ile Asn Leu
            900                 905                 910

Met Lys Arg Leu Leu Cys Arg Leu Pro Glu Val Arg Ile Gly Cys Ser
        915                 920                 925

Ile Asn Gly Tyr Lys Asp Ile Lys Glu His Ala Phe Phe Gly Asp Phe
    930                 935                 940

Asp Trp Asp Lys Leu Ala Gly Arg Gly Leu Pro Pro Leu Ala Pro
945                 950                 955                 960

Lys Gly Glu Thr Tyr Ala Glu Asp Thr Glu Gln Ser Ser Phe Glu Leu
                965                 970                 975

Asp Glu Asp Asp Thr Ile Val Leu Glu Asp Glu Tyr Asp Trp Asp Lys
            980                 985                 990

Asp Phe

<210> SEQ ID NO 14
<211> LENGTH: 22
<212> TYPE: DNA
<213> ORGANISM: Artificial Sequence
<220> FEATURE:
<223> OTHER INFORMATION: PKG
<220> FEATURE:
<221> NAME/KEY: misc_feature
<222> LOCATION: (1)...(22)
<223> OTHER INFORMATION: n = A,T,C or G

<400> SEQUENCE: 14

-continued

```
acnggncanc cngaagcaag ca                                              22

<210> SEQ ID NO 15
<211> LENGTH: 26
<212> TYPE: DNA
<213> ORGANISM: Artificial Sequence
<220> FEATURE:
<223> OTHER INFORMATION: PKG
<220> FEATURE:
<221> NAME/KEY: misc_feature
<222> LOCATION: (1)...(26)
<223> OTHER INFORMATION: n = A,T,C or G

<400> SEQUENCE: 15
gcnaagagaa cttgnctgag ttcttc                                          26

<210> SEQ ID NO 16
<211> LENGTH: 28
<212> TYPE: DNA
<213> ORGANISM: Artificial Sequence
<220> FEATURE:
<223> OTHER INFORMATION: PKG
<220> FEATURE:
<221> NAME/KEY: misc_feature
<222> LOCATION: (1)...(28)
<223> OTHER INFORMATION: n = A,T,C or G

<400> SEQUENCE: 16
gaaggactac ncaaggcnga aggactgc                                        28
```

TOXOPLASMA GONDII CYLCLIC GMP DEPENDENT PROTEIN KINASE G AS A CHEMOTHERAPEUTIC TARGET FOR ANTIPROTOZOAL AGENTS

CROSS-REFERENCE TO RELATED APPLICATIONS

This application is a divisional application of U.S. application Ser. No. 10/348,155, filed Jan. 21, 2003, now U.S. Pat. No. 7,125,700, which is a divisional application of U.S. application Ser. No. 09/521,511, filed Mar. 8, 2000, now U.S. Pat. No. 6,555,358, which claims the benefit of priority from U.S. Provisional Application Ser. No. 60/129,058, filed Apr. 13, 1999.

SUMMARY OF THE INVENTION

The present invention relates to a novel protein kinase which may be used as a chemotherapeutic target for antiprotozoal agents. The invention further concerns a method for identifying potential antiprotozoal agents using the novel kinase, as well as a method for treating protozoal infections using a substance that inhibits the action of said kinase.

BACKGROUND OF THE INVENTION

Parasitic protozoa are responsible for a wide variety of infections in man and animals. Many of the diseases are life threatening to the host, and in animal husbandry, can cause considerable economic loss. For example, malaria remains a significant health threat to humans despite massive international attempts to eradicate the disease; trypanosomiasis such as Chagas disease caused by *Trypanosoma cruzi* and African sleeping sickness caused by *T. brucei* are not uncommon in South America and Africa, respectively; and opportunistic infections in immunocompromised hosts caused by *Pneumocystis carinii, Toxoplasma gondii, Cryptosporidium* sp. are becoming increasingly significant in the developed countries.

Coccidiosis, a widespread disease of domesticated animals, is caused by protozoal infection. In the poultry industry, coccidiosis is responsible for high levels of morbidity and mortality in the bird population and may result in extreme economic losses. The infectious agents are protozoa of the genus *Eimeria*. Some of the most significant avian *Eimeria* species include *E. tenella, E. acervulina, E. necatrix, E. brunetti* and *E. maxima*.

In some protozoal diseases, such as Chagas disease, there is no satisfactory treatment; in others, drug-resistant strains of the protozoa may develop. Accordingly, there exists a continued need to identify new and effective anti-protozoal drugs. However, antiparasitic drug discovery has been, for the most part, a random and laborious process through biological screening of natural products and synthetic compounds against a panel of parasites. This process can be greatly facilitated and made more specific if a biochemical target of antiprotozoal drugs can be identified, and incorporated into the screening process.

cGMP dependent protein kinases (PKG) catalyze the phosphorylation of specific protein substrates. In the absence of cGMP the activity of these enzymes is very low. In mammalian cells there are two types of PKG, a soluble (PKG1) and a membrane bound form (PKG2). Multiple splice variants of the soluble protein have been identified. PKGs are known to control many cellular processes in higher animals. Mammalian PKG1 is most abundant in smooth muscle, platelets and cerebellum. Targeted disruption of PKG1 in mice generated phenotypes clearly associated with smooth muscle, namely severe intestinal and vascular dysfunctions. PKG2 expression is highest in the small intestine, several regions of the brain (particularly the hypothalamus) and lung. Transgenic mice lacking PKG2 display a dwarfed phenotype caused by defects in ossification at the growth plates and also have intestinal secretion dysfunctions. PKGs have also been identified in *Dictyostelium, Paramecium, Tetrahymena* and *Ascaris*.

DETAILED DESCRIPTION OF THE INVENTION

In one aspect the present invention provides a novel protozoal cGMP dependent protein kinase (PKG) and a polynucleotide sequence encoding the PKG polypeptide. In one embodiment, the invention provides a PKG purified fraction of *Eimeria tenella* consisting essentially of the amino acid sequence of SEQ ID NO: 11, and the polynucleotide sequence encoding the polypeptide of SEQ ID NO: 11. More specifically, the polynucleotide sequences is as set forth in SEQ ID NO: 10. In another embodiment, the invention provides a substantially pure PKG of *Toxoplasma gondii* consisting essentially of the amino acid sequence of SEQ ID NO: 13, and the polynucleotide sequence encoding the polypeptide of SEQ ID NO: 13. More specifically, the polynucleotide sequences is as set forth in SEQ ID NO: 12.

In another aspect the present invention provides a method for identifying compounds having antiprotozoal activity comprising:

(a) contacting protozoal PKG with, (i) a known amount of a labeled compound that interacts with a PKG and, (ii) a known dilution of a test compound or a natural product extract; and (b) quantitating the percent inhibition of interaction of said labeled compound induced by said test compound.

In another aspect the present invention provides a method for identifying compounds having antiprotozoal activity comprising:

(a) contacting an intact host or protozoal cell with a test compound or a natural product extract;

(b) disrupting said cell to obtain a biochemical fraction possessing PKG catalytic activity; and (c) determining the level of PKG activity in said biochemical fraction.

The methods of the invention provides a facile and specific assay to screen compounds as potential antiprotozoal drugs.

Polypeptides

The novel PKG of the present invention is of protozoal origin; in particular the enzyme is present in, but not restricted to, protozoa of the apicomplexan family, and more specifically in *Eimeria* sp. The native *Eimeria tenella* PKG of the present invention is a protein of about 120 kDa, and having about 1,003 amino acids. The native PKG from *Toxoplasma gondii* is approximately 115 kDa and having about 994 amino acids. The PKG of the present invention includes a crude extract of the soluble protein, a PKG purified fraction isolated from a protozoan parasite (native enzyme), affinity purified native PKG (purified from a soluble extract using cGMP, substrate based peptides, inhibitor based molecules or antibodies) as well as a PKG produced by recombinant DNA technology (recombinant expressed enzyme). The term "PKG purified fraction" as used herein, refers to a PKG polypeptide which is free of most other proteins, lipids, carbohydrates, nucleic acids, or other materials with which it is naturally associated. One skilled in the art can purify PKG using standard techniques for protein purification. The PKG purified fraction will yield a major band on a reducing polyacrylamide gel. The sequence of the polypeptide can be determined by amino acid sequencing.

The protozoal PKGs of the present invention include a polypeptide of SEQ ID NO: 11, and a polypeptide of SEQ ID NO:13, as well as functional polypeptides and fragments thereof. As used herein, the term "functional polypeptides and fragments" refers to a polypeptide which possesses PKG activity. Minor modifications of the PKG primary amino acid sequence may result in proteins which have substantially equivalent activity as compared to the PKG polypeptide described herein. Such modifications may be deliberate, as by site-directed mutagenesis, or may be spontaneous. All of the polypeptides produced by these modifications are included herein as long as the enzymatic activity of PKG is present. Further, deletion of one or more amino acids can also result in a modification of the structure of the resultant molecule without significantly altering its kinase activity. This can lead to the development of a smaller active molecule which may have broader utility. For example, it is possible to remove amino or carboxyl terminal amino acids which may not be required for kinase activity. Smaller peptides containing the biological activity of PKG are included in the invention.

The PKG polypeptide of the invention also includes conservative variations of the polypeptide sequence which do not substantially alter the biological activity of the protein. The term "conservative variation" as used herein denotes the replacement of an amino acid residue by another, biologically similar residue. Examples of conservative variations include the substitution of one hydrophobic residue such as isoleucine, valine or leucine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that the activity of the enzyme is not substantially altered.

Polynucleotides

The invention also provides isolated polynucleotide sequences consisting essentially of a polynucleotide sequence encoding a polypeptide having the amino acid sequence of SEQ ID NO:11 or SEQ ID NO:13. As used herein, "polynucleotide" refers to a polydeoxyribonucleotides or polyribonucleotides, in the form of a separate fragment or a larger construct, and includes DNA, cDNA and RNA sequences which encode protozoal PKG. The term "isolated" as used herein includes polynucleotides substantially free of other nucleic acids, proteins, lipids, carbohydrates or other materials with which it is naturally associated. It is understood that all polynucleotides encoding all or a portion of protozoal PKG are also included herein, as long as they encode a polypeptide with PKG kinase activity. Such polynucleotides include naturally occurring, synthetic, and intentionally manipulated polynucleotides. For example, PKG polynucleotide may be subjected to site-directed mutagenesis.

It is known that there is a substantial amount of redundancy in the various codons which code for specific amino acids. There are 20 natural amino acids, most of which are specified by more than one codon. Therefore, this invention is also directed to those DNA sequences which contain alternative codons which code for the eventual translation of the identical amino acid. For purposes of this specification, a sequence bearing one or more replaced codons will be defined as a degenerate variation. Therefore, the present invention discloses codon redundancy which may result in differing DNA molecules expressing an identical protein.

Specifically disclosed herein is a cDNA sequence 4283 base pair (bp) in length (SEQ. ID NO:10) containing the predicted coding region for E. tenella PKG. The cDNA includes an open reading frame of 3009 base pairs encoding a protein of about 1003 amino acids, having a deduced molecular weight of about 113 kDa. Also specifically disclosed herein is a cDNA sequence 3898 base pair (bp) in length (SEQ. ID NO:12) containing the predicted coding region for T. gondii PKG. The cDNA includes an open reading frame of 2982 base pairs encoding a protein of about 994 amino acids, having a deduced molecular weight of about 112 kDa. The polynucleotides encoding PKG include the nucleotide sequences SEQ ID NO:10 and SEQ ID NO:12, as well as nucleic acid sequences complementary to that sequence. A complementary sequence may include an antisense nucleotide. When the sequence is RNA, the deoxynucleotides A, G, C, and T are replaced by ribonucleotides A, G, C, and U, respectively. Also included in the invention are fragments of the above-described nucleic acid sequences that are at least 15 bases in length, which is sufficient to permit the fragment to selectively hybridize to DNA that encodes the proteins of the present invention including PKG of SEQ ID NO:11 and SEQ ID NO:13.

Any of a variety of procedures may be used to clone PKG. These methods include, but are not limited to, (1) a RACE PCR cloning technique (Frohman, et al., 1988, Proc. Natl. Acad. Sci. 85: 8998-9002). 5' and/or 3' RACE may be performed to generate a full length cDNA sequence. This strategy involves using gene-specific oligonucleotide primers for PCR amplification of PKG cDNA. These gene-specific primers are designed through identification of an expressed sequence tag (EST) nucleotide sequence which has been identified by searching any number of publicly available nucleic acid and protein databases;

(2) direct functional expression of the PKG cDNA following the construction of a PKG-containing cDNA library in an appropriate expression vector system;

(3) screening a PKG-containing cDNA library constructed in a bacteriophage or plasmid vector with a labeled degenerate oligonucleotide probe designed from the amino acid sequence of the PKG protein;

(4) screening a PKG-containing cDNA library constructed in a bacteriophage or plasmid vector with a partial cDNA encoding the PKG protein. This partial cDNA is obtained by the specific PCR amplification of PKG DNA fragments through the design of degenerate oligonucleotide primers from the amino acid sequence known for other kinases which are related to the PKG protein;

(5) screening a PKG-containing cDNA library constructed in a bacteriophage or plasmid vector with a partial cDNA encoding the PKG protein. This strategy may also involve using gene-specific oligonucleotide primers for PCR amplification of PKG cDNA identified as an EST as described above; or (6) designing 5' and/or 3' gene specific oligonucleotides using SEQ ID NO:10 or SEQ ID NO:12 as a template so that either the full length cDNA may be generated by known RACE techniques, or a portion of the coding region may be generated by these same known RACE techniques to generate and isolate a portion of the coding region to use as a probe to screen one of numerous types of cDNA and/or genomic libraries in order to isolate a full length version of the nucleotide sequence encoding PKG.

It is readily apparent to those skilled in the art that suitable cDNA libraries may be prepared from cells or cell lines which have PKG activity. The selection of cells or cell lines for use in preparing a cDNA library to isolate a PKG cDNA may be done by first measuring cell associated PKG activity using any known assay for PKG activity.

Preparation of cDNA libraries can be performed by standard techniques well known in the art. Well known cDNA library construction techniques can be found for example, in Sambrook, et al., 1989, *Molecular Cloning: A Laboratory Manual;* Cold Spring Harbor Laboratory, Cold Spring Harbor, N.Y. Complementary DNA libraries may also be obtained from numerous commercial sources, including but not limited to Clontech Laboratories, Inc. and Stratagene.

It is also readily apparent to those skilled in the art that DNA encoding PKG may also be isolated from a suitable genomic DNA library. Construction of genomic DNA libraries can be performed by standard techniques well known in the art. Well known genomic DNA library construction techniques can be found in Sambrook, et al., supra. Genomic DNA libraries may also be obtained from numerous commercial sources, including but not limited to Clontech Laboratories, Inc. and Stratagene.

In order to clone the PKG gene by one of the preferred methods, the amino acid sequence or DNA sequence of PKG or a homologous protein may be necessary. To accomplish this, the PKG or a homologous protein may be purified and partial amino acid sequence determined by automated sequenators. It is not necessary to determine the entire amino acid sequence, but the linear sequence of two regions of 6 to 8 amino acids can be determined for the PCR amplification of a partial PKG DNA fragment. Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the PKG sequence but others in the set will be capable of hybridizing to PKG DNA even in the presence of DNA oligonucleotides with mismatches. The mismatched DNA oligonucleotides may still sufficiently hybridize to the PKG DNA to permit identification and isolation of PKG encoding DNA.

Alternatively, the nucleotide sequence of a region of an expressed sequence may be identified by searching one or more available databases. Gene-specific primers may be used to perform PCR amplification of a cDNA of interest from either a cDNA library or a population of cDNAs. As noted above, the appropriate nucleotide sequence for use in a PCR-based method may be obtained from SEQ ID NO:10 or SEQ ID NO:12, either for the purpose of isolating overlapping 5' and 3' RACE products for generation of a full-length sequence coding for PKG, or to isolate a portion of the nucleotide sequence coding for PKG for use as a probe to screen one or more cDNA- or genomic-based libraries to isolate a full-length sequence encoding PKG or PKG-like proteins.

DNA sequences of the invention can be obtained by several methods. For example, the DNA can be isolated using hybridization techniques which are well known in the art. These include, but are not limited to: 1) hybridization to genomic or cDNA libraries with probes to detect homologous nucleotide sequences; 2) antibody screening of expression libraries to detect cloned DNA fragments with shared structural features; and 3) PCR amplification of a desired nucleotide sequence using oligonucleotide primers. Preferably the PKG polynucleotide of the invention is derived from a protozoal organism, and most preferably from an *Eimeria* species. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known.

The DNA sequence encoding the protein can be deduced from the genetic code; however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., Nucl. Acid Res., 9:879, 1981).

The development of specific DNA sequences encoding PKG can also be obtained by: 1) isolation of double-stranded DNA sequences from genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form.

A preferred method for obtaining genomic DNA for example is the Polymerase Chain Reaction (PCR), which relies on an in vitro method of nucleic acid synthesis by which a particular segment of DNA is specifically replicated. Two oligonucleotide primers that flank the DNA fragment to be amplified are utilized in repeated cycles of heat denaturation of the DNA, annealing of the primers to their complementary sequences, and extension of the annealed primers with DNA polymerase. These primers hybridize to opposite strands of the target sequence and are oriented so that DNA synthesis by the polymerase proceeds across the region between the primers. Since the extension products themselves are also complementary to and capable of binding primers, successive cycles of amplification essentially double the amount of the target DNA synthesized in the previous cycle. The result is an exponential accumulation of the specific target fragment, approximately $2^{<n>}$, where n is the number of cycles of amplification performed (see PCR Protocols, Eds. Innis, et al., Academic Press, Inc., 1990, incorporated herein by reference).

A cDNA expression library, in a vector such as lambda gt11, can be screened indirectly for PKG peptides having at least one epitope, using antibodies specific for PKG. Such antibodies can be either polyclonally or monoclonally derived and used to detect an expression product indicative of the presence of a PKG cDNA. The polynucleotide sequence for PKG also includes sequences complementary to the polynucleotide encoding PKG (antisense sequences). Antisense nucleic acids are DNA or RNA molecules that are complementary to at least a portion of a specific mRNA molecule (Weintraub, Scientific American, 262:40, 1990). The invention embraces all antisense polynucleotides capable of inhibiting the production of the PKG polypeptide. In the cell, the antisense nucleic acids hybridize to the corresponding mRNA, forming a double-stranded molecule. The antisense nucleic acids may interfere with the translation of the mRNA since the cell will not translate a mRNA that is double-stranded, or alternatively, the double-stranded mRNA is targeted for degradation. Antisense oligomers of about 15 nucleotides are preferred, since they are easily synthesized, small enough to enter the cell, and are less likely to cause problems than larger molecules when introduced into the target PKG-producing cell. The use of antisense methods to inhibit the translation of genes is well known in the art (Marcus-Sakura, Anal. Biochem., 172:289, 1988).

Vectors, Host Cells, Expression

DNA sequences encoding PKG can be expressed in vitro by DNA transfer into a suitable host cell. "Host cells" are cells in which a vector carrying DNA sequences of interest can be propagated and the protein coded for by the DNA sequences can be expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

A variety of expression vectors may be used to express recombinant PKG in host cells. "Expression vectors" are DNA sequences that are required for the transcription of cloned DNA and the translation of their mRNAs in an appropriate host. Such vectors can be used to express eukaryotic DNA in a variety of hosts such as bacteria, blue green algae, plant cells, insect cells, apicomplexan parasites and animal cells. Specifically designed vectors allow the shuttling of DNA between hosts such as bacteria-yeast, bacteria-insect cells, bacteria-apicomplexan parasites or bacteria-animal cells. An appropriately constructed expression vector should contain: an origin of replication for autonomous replication in host cells, selectable markers, a limited number of useful restriction enzyme sites, a potential for high copy number, and active promoters. Other expression vectors do not contain an origin of replication for autonomous replication in host cells but rather depend on the ability of the vector to stably integrate (either randomly or by a homologous integration event) using a marker to select for integration/maintenance. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

Commercially available mammalian expression vectors which may be suitable for recombinant PKG expression, include but are not limited to, pcDNA3, pcDNA3.1, pcDNAI, pcDNAIamp (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and λZD35 (ATCC 37565).

A variety of bacterial expression vectors may be used to express recombinant PKG in bacterial cells. Commercially available bacterial expression vectors which may be suitable for recombinant PKG expression include, but are not limited to pCR2.1 (Invitrogen), pET11a (Novagen), lambda gt11 (Invitrogen), pcDNAII (Invitrogen), pKK223-3 (Pharmacia), and pQE vectors (Qiagen).

A variety of fungal cell expression vectors may be used to express recombinant PKG in fungal cells. Commercially available fungal cell expression vectors which may be suitable for recombinant PKG expression include but are not limited to pYES2 (Invitrogen), *Pichia* expression vector (Invitrogen).

A variety of insect cell expression vectors may be used to express recombinant PKG in insect cells. Commercially available insect cell expression vectors which may be suitable for recombinant expression of PKG include but are not limited to pBlueBacIII, pBlueBacHis2 (Invitrogen) and pFastBac1, pFastBacHT (Life Technologies).

A variety of expression vectors may be used to express recombinant PKG in apicomplexan parasites, most notably *Toxoplasma gondii*. Expression vectors which may be suitable for recombinant expression of PKG include but are not limited to pminCAT/HXGPRT−, pDHFR-TSc3/M3, pDHFR-TSc3/M2M3, pminiHXGPRT, and pminP30/G (NIH AIDS Research and Reference Reagent Program).

The expression vector may be introduced into host cells via any one of a number of techniques including but not limited to infection, transformation, transfection, lipofection, protoplast fusion, and electroporation. The expression vector-containing cells are clonally propagated and individually analyzed to determine whether they produce PKG protein. Identification of PKG expressing host cell clones may be done by several means, including but not limited to immunological reactivity with anti-PKG antibodies.

Expression of PKG DNA may also be performed using in vitro produced synthetic mRNA or native mRNA. Synthetic mRNA or mRNA isolated from PKG producing cells can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

A variety of host-expression vector systems may be utilized to express the PKG coding sequence. These include but are not limited to microorganisms such as bacteria transformed with recombinant bacteriophage DNA, plasmid DNA or cosmid DNA expression vectors containing the PKG coding sequence; yeast transformed with recombinant yeast expression vectors containing the PKG coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the PKG coding sequence; insect cell systems infected with recombinant virus expression vectors (e.g., baculovirus) containing the PKG coding sequence; or animal cell systems infected with recombinant virus expression vectors (e.g., retroviruses, adenovirus, vaccinia virus) containing the PKG coding sequence, or transformed animal cell systems engineered for stable expression.

To determine the PKG cDNA sequence(s) that yields optimal levels of PKG protein, PKG cDNA molecules including but not limited to the following can be constructed: the full-length open reading frame of the PKG cDNA and various constructs containing portions of the cDNA encoding only specific domains of the protein or rearranged domains of the protein. All constructs can be designed to contain none, all or portions of the 5' and/or 3' untranslated region of PKG. PKG activity and levels of protein expression can be determined following the introduction, both singly and in combination, of these constructs into appropriate host cells. Following determination of the PKG cDNA cassette yielding optimal expression in transient assays, this PKG cDNA construct is transferred to a variety of expression vectors (including recombinant viruses), including but not limited to those for mammalian cells, plant cells, insect cells, oocytes, bacteria, and yeast cells.

The protein coding region of the recombinant PKG coding sequence may also be modified at the level of the cDNA to add epitope tags. Modification of the cDNA sequence is usually but not exclusively directed to the amino- or carboxy-terminal end of the protein coding region. This is accomplished by any of several methods common in the art. Examples of modifications include but are not limited to the influenza viral HA tag, the FLAG tag, a hexahistidine tag, the c-myc tag, as well as fusions with maltose binding protein, glutathione transferase and green fluorescent protein. These tags can serve as a means to distinguish recombinant PKG from host PKG immunologically using commercially available antisera to the tag sequences and as a purification tool to resolve recombinant from host PKGs.

Levels of recombinant PKG protein in host cells is quantified by a variety of techniques including, but not limited to, immunoaffinity and/or ligand affinity techniques. PKG-specific affinity beads or PKG-specific antibodies are used to isolate PKG protein metabolically labeled with radioactive amino acids such as [$^3$H]-leucine or [$^{35}$S]-methionine or unlabelled PKG protein. Labeled PKG protein is analyzed by SDS-PAGE. Unlabelled PKG protein is detected by Western blotting, ELISA or RIA assays employing PKG-specific or epitope tag-specific antibodies.

Purification of PKG

Following expression of PKG in a host cell, PKG protein may be recovered to provide PKG in active form. Several PKG purification procedures are available and suitable for use. Recombinant PKG may be purified from cell lysates and extracts, or from conditioned culture medium, by various combinations of, or individual application of salt fractionation, ion exchange chromatography, size exclusion chromatography, hydroxyapatite adsorption chromatography, hydrophobic interaction chromatography and cyclic nucleotide affinity chromatography.

In addition, recombinant PKG can be separated from other cellular proteins by use of an immuno-affinity column made with monoclonal or polyclonal antibodies specific for full length PKG, or polypeptide fragments of PKG. Additionally, polyclonal or monoclonal antibodies may be raised against a synthetic peptide (usually from about 9 to about 25 amino acids in length) from a portion of the protein.

Monospecific antibodies to PKG are purified from mammalian antisera containing antibodies reactive against PKG or are prepared as monoclonal antibodies reactive with PKG using the technique of Kohler and Milstein (1975, *Nature* 256: 495-497). Monospecific antibody as used herein is defined as a single antibody species or multiple antibody species with homogenous binding characteristics for PKG. Homogenous binding as used herein refers to the ability of the antibody species to bind to a specific antigen or epitope, such as those associated with the PKG, as described above. PKG specific antibodies are raised by immunizing animals such as mice, rats, guinea pigs, rabbits, goats, horses and the like, with an appropriate concentration of PKG or PKG synthetic peptide either with or without an immune adjuvant.

Preimmune serum is collected prior to the first immunization. Each animal receives between about 0.1 µg and about 1000 µg of PKG associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of the PKG protein or PKG synthetic peptide in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal or smaller amount of PKG in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with PKG are prepared by immunizing inbred mice, preferably Balb/c, with PKG. The mice are immunized by the IP or SC route with about 1 µg to about 100 µg, preferably about 10 µg, of PKG in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 1 to about 100 µg of the same PKG antigen in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) using PKG as the antigen. The culture fluids are also tested in the Ouchterlony precipitation assay to determine the isotype of the mAb. Hybridoma cells from antibody positive wells are cloned by a technique such as the soft agar technique of MacPherson, 1973, Soft Agar Techniques, in *Tissue Culture Methods and Applications*, Kruse and Paterson, Eds., Academic Press.

Monoclonal antibodies are produced in vivo by injection of pristine primed Balb/c mice, approximately 0.5 ml per mouse, with about $2 \times 10^6$ to about $6 \times 10^6$ hybridoma cells about 4 days after priming. Ascites fluid is collected at approximately 8-12 days after cell transfer and the monoclonal antibodies are purified by techniques known in the art.

In vitro production of anti-PKG monoclonal antibody is carried out by growing the hydridoma in DMEM containing about 2% fetal calf serum to obtain sufficient quantities of the specific monoclonal antibody. The monoclonal antibodies are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of PKG in body fluids or tissue and cell extracts.

It is readily apparent to those skilled in the art that the above described methods for producing monospecific antibodies may be utilized to produce antibodies specific for PKG polypeptide fragments, or full-length PKG polypeptide.

PKG antibody affinity columns are made by adding the antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) and the cell culture supernatants or cell extracts containing PKG or PKG fragments are slowly passed through the column. The column is then washed with phosphate buffered saline until the optical density ($A_{280}$) falls to background, then the protein is eluted with 0.23 M glycine-HCl (pH 2.6). The purified PKG protein is then dialyzed against phosphate buffered saline.

One skilled in the art will appreciate that the above described procedures for purification of recombinant expressed PKG are also suitable for purification of the native enzyme from a protozoan parasite.

Inhibitors—Assays and Molecules

In another aspect of the present invention there is provided a method for identifying compounds having antiprotozoal activity. In one embodiment said method comprises:

(a) contacting protozoal PKG with (i) a known amount of a labeled compound that interacts with a PKG and (ii) a known dilution of a test compound or a natural product extract; and (b) quantitating the percent inhibition of interaction of said labeled compound induced by said test compound.

The PKG may be a purified or partially purified native enzyme, a cloned PKG or an engineered variant thereof, a crude preparation of the enzyme, or an extract containing PKG activity. Fragments of PKG that retain the desired enzyme activity are also within the scope of the invention.

A compound that interacts with PKG may be one that is a substrate for the enzyme, or one that binds to the enzyme either at its active site or at an alternate site (e.g., the cGMP binding domains) that results in altered enzyme activity. A substrate may be a generic protein kinase substrate (e.g., myosin basic protein, MBP), a synthetic peptide or other naturally occurring substrates. Examples of compounds that bind to PKG are known inhibitors such as KT5823, synthetic or naturally occurring peptides as well as other small molecule (i.e. non-peptidyl) inhibitors such as 2-(4-fluorophenyl)-5-(N-methylpiperidin-4-yl)-3-(4-pyridyl)pyrrole, which will be referred to herein as "Inhibitor Compound". The Inhibitor Compound and its preparation are disclosed in U.S. Pat. No. 5,792,778. The compound that interacts with PKG is preferably labeled to allow easy quantitation of the level of interaction between the compound and the enzyme. Preferred radiolabels are [$^{14}$C] or [$^{3}$H]. The tritiated Inhibitor Compound may be prepared as follows:

A solution of Inhibitor Compound (as the free amine, 2.5 mg, 0.007 mmol) in DMSO (0.8 ml) was stirred for half-hour at room temperature. High specific activity tritium labeled methyl iodide (200 mCi, 0.0026 mmol, at 80 Ci/mmol in 0.4 ml toluene solution) was added to this mixture and the resulting clear solution was stirred for 24 hour. The product was diluted with isopropanol (35 mL) evaporated to near dryness and dissolved with 3 mL of methanol for HPLC purification. The product was collected into a vial containing 7 mL of cold water (chilled in the refrigerator before use). After assay for radioactivity and radio-purity, the sample was stored in the refrigerator to prevent decomposition. Total activity of the purified product was 45 mCi and at specific activity of 68 Ci/mmol (by UV spectrum measurement). HPLC conditions are: Zorbax SB-C18 Semi-prep column (5 um, 9.4 mmI.D.× 250 mm), 65/35/0.1 (v/v/v) water/acetonitrile/HClO4. UV-detection at 230 nm, 4.5 mL/min, Rt=24.5 min, radiochemical purity: 98.5%

The test compound may be a synthetic compound, a purified preparation, crude preparation, or an initial extract of a natural product obtained from plant, microorganism or animal sources.

One particular embodiment of the present method is based on test compound induced inhibition of PKG activity. The enzyme inhibition assay involves adding PKG or an extract containing PKG to mixtures of enzyme substrates (one of which is radiolableled) and the test compound, each of which are present in known concentrations. The amount of the enzyme is chosen such that less than 20% of the radiolabeled substrate (usually [$^{32}$P]- or [$^{33}$P]-ATP,) is consumed during the assay. The assay is carried out with the test compound at a series of different dilution levels. After a period of incubation, the labeled portion of the ATP substrate becomes covalently attached by enzymatic action to the peptide or protein substrate. This reaction product is separated from unincorporated precursor and counted. The assay is generally carried out in parallel with a control (no test compound) and a positive control (containing a known enzyme inhibitor instead of a test compound). The concentration of the test compound at which 50% of the enzyme activity is inhibited ($IC_{50}$) is determined using a recognized method.

Although enzyme inhibition is the most direct measure of the inhibitory activity of the test compound, the present inventors have found that results obtained from competitive binding assay in which the test compound competes with a known inhibitor for binding to the enzyme active site correlate well with the results obtained from enzyme inhibition assay described above. Accordingly, another particular embodiment of the present method is based on competitive binding of test compound and a known PKG inhibitor. The binding assay represents a more convenient way to assess enzyme inhibition since it allows the use of a crude extract containing PKG rather than partially purified enzyme. The use of a crude extract may not always be suitable in the enzyme inhibition assay because other enzymes present in the extract may phosphorylate the test substrate. The competition binding assay is carried out by adding the PKG or an extract containing PKG activity to a mixture of the test compound and a labeled inhibitor, both of which are present in the mixture in known concentrations. After incubation, the enzyme-inhibitor complex is separated from the unbound labeled inhibitors and unlabeled test compound, and counted. The concentration of the test compound required to inhibit 50% of the binding of the labeled inhibitor to the PKG ($IC_{50}$) is calculated.

In a preferred embodiment, the method of the present invention utilizes a recombinant PKG, a native PKG, or an extract containing PKG obtained from a protozoal source, such as *Eimeria, Toxoplasma* or *Plasmodium* sp.

In a more preferred embodiment, the method of the present invention further comprises determining the $IC_{50}$ of test compounds against host PKG in either the enzyme inhibition assay or the binding assay as described above, to identify those compounds that have selectivity for parasitic PKG over that of a host. The assays are the same as previously described, with the PKG activity obtained from a host of protozoa; for example the host PKG may be obtained from a mammalian source, e.g. human, or an avian source, e.g. chicken.

Another method useful to identify inhibitors that are selective for parasitic PKG is the use of an in gel kinase assay to determine the level of substrate phosphorylation catalyzed by parasite PKG relative to host PKG or other cellular kinase activities. Thus compounds that specifically inhibit phosphorylation of a test substrate (e.g., myelin basic protein) by parasite PKG and not a host PKG, would be considered selective parasitic PKG inhibitors.

Where the enzyme inhibition or binding assay utilizes a crude preparation or an extract containing PKG, the target of the test compound may be verified by examining the level of native substrate phosphorylation. Thus, the intact host or parasitic cell containing the enzyme is treated with the test compound. Alternatively, intact host or parasite cells containing the enzyme are treated with test compound in the presence of labeled phosphate ($[^{33}P]$ or $[^{32}P]$ is the preferred label). In both cases the cells are lysed, soluble proteins are partially purified, and analyzed by two dimensional polyacrylamide electrophoresis. Proteins are detected by staining or by detection of radiolabel by autoradiography or fluorography. Differentially phosphorylated species can readily be distinguished on such gels due to the altered migration of multiply phosphorylated proteins or by the presence/absence of an autoradiographic signal. A PKG inhibitor will block the incorporation of radiolabeled phosphate into substrate. Since this technique uses intact cells treated with the test compound, this technique may also be used to identify prodrugs that may be converted to a PKG inhibitor within the cellular environment, but may not be so identified by assay based on the enzyme itself.

Another embodiment of the method for identifying compounds having antiprotozoal activity comprises:

(a) contacting an intact host or protozoal cell with a test compound or a natural product extract;

(b) disrupting said cell to obtain a biochemical fraction possessing PKG catalytic activity; and (c) determining the level of PKG activity in said biochemical fraction.

Thus intact host cell(s) are treated with a test compound at a known concentration (or a natural product extract at know dilution) for 1 minute to 12 hours. Thereafter the host cells are lysed, for example, using the method described in Example 3 or other known methods in the art. The level of PKG catalytic activity may be determined using methods hereinafter described in the Examples as well as other methods generally known by those skilled in the art.

Compounds identified as PKG inhibitors may be useful as antiprotozoal agents, and as such, they may be used in the treatment and prevention of protozoal diseases in human and animals, including poultry. Thus, PKG inhibitors may be administered to a host suffering from a protozoal infection a therapeutically effective amount of a compound which inhibits PKG. A therapeutically effective amount may be one that is sufficient to inhibit PKG of the causative protozoa. Examples of protozoal diseases against which PKG inhibitors may be used, and their respective causative pathogens, include: 1) amoebiasis (*Dientamoeba* sp., *Entamoeba histolytica*); 2) giardiasis (*Giardia lamblia*); 3) malaria (*Plasmodium* species including *P. vivax, P. falciparum, P. malariae* and *P. ovale*); 4) leishmaniasis (*Leishmania* species including *L. donovani, L tropica, L. mexicana,* and *L. braziliensis*); 5) trypanosomiasis and Chagas disease (*Trypanosoma* species including *T. brucei, T. theileri, T. rhodesiense, T. gambiense, T. evansi, T. equiperdum, T. equinum, T. congolense, T. vivax* and *T. cruzi*); 6) toxoplasmosis (*Toxoplasma gondii*); 7) neosporosis (*Neospora caninum*); 8) babesiosis (*Babesia* sp.); 9) cryptosporidiosis (*Cryptosporidium* sp.); 10) dysentary (*Balantidium coli*); 11) vaginitis (*Trichomonas* species including *T. vaginitis*, and *T. foetus*); 12) coccidiosis (*Eimeria* species including *E. tenella, E. necatrix, E. acervulina, E. maxima, E. brunetti, E. mitis, E. bovis, E. melagramatis,* and *Isospora* sp.); 13) enterohepatitis (*Histomonas gallinarum*), and 14) infections caused by *Anaplasma* sp., *Besnoitia* sp., *Leucocytozoan* sp., *Microsporidia* sp., *Sarcocystis* sp., *Theileria* sp., and *Pneumocystis carinii*.

PKG inhibitors are preferably used in the treatment or prevention of protozoal infections caused by a member of the sub-phyllum Apicomplexa. PKG inhibitors are also preferably used in the treatment or prevention of malaria, toxoplasmosis, cryptosporidiosis and trypanosomiasis in humans and animals; and in the management of coccidiosis, particularly in poultry, either to treat coccidial infection or to prevent the occurrence of such infection.

In the case that a PKG inhibitor is expected to be administered on a chronic basis, such as in the prevention of coccidiosis in poultry, the PKG inhibitor preferably is selective for protozoal over the host PKG activity. Long term administration of such a selective inhibitor would minimize adverse effects to the host due to PKG inhibition.

Two specific examples of using PKG inhibitors to prevent the establishment of parasitic infections in humans and animals are 1) the prevention of *Plasmodium* (malaria) infection in humans in endemic areas and 2) the prevention of coccidiosis in poultry by administering the compound continuously in the feed or drinking water. Malaria is the number one cause of death in the world. The disease is transmitted by mosquitoes in endemic areas and can very rapidly progress to a life threatening infection. Therefore, individuals living in or visiting areas where malaria carrying mosquitoes are present routinely take prophylactic drugs to prevent infection. The PKG inhibitor would be administered orally or parenterally one or more time(s) a day. The dose would range from 0.01 mg/kg to 100 mg/kg. The compound could be administered for the entire period during which the patient or animal is at risk of acquiring a parasitic infection.

Coccidiosis is a disease which can occur in humans and animals and is caused by several genera of coccidia. The most economically important occurrence of coccidiosis is the disease in poultry. Coccidiosis in poultry is caused by protozoal parasites of the genus *Eimeria*. The disease can spread quite rapidly throughout flocks of birds via contaminated feces. The parasites destroy gut tissue and therefore damage the gut lining impairing nutrient absorption. An outbreak of coccidiosis in a poultry house can cause such dramatic economic losses for poultry producers that it has become standard practice to use anticoccidial agents prophylactically in the feed. A PKG inhibitor would be administered in the feed or drinking water for a portion of, or the entire life of the birds. The dose would range between 0.1 ppm to 500 ppm in the feed or water.

For treatment of established parasitic infections in humans or animals, the PKG inhibitor could be administered orally or parenterally once the infection is suspected or diagnosed. The treatment period would vary according to the specific parasitic disease and the severity of the infection. In general the treatment would be continued until the parasites were eradicated and/or the symptoms of the disease were resolved. Two specific examples are the treatment of a 1) *Cryptosporidium parvum* infection in an animal or human and treatment of acute *Plasmodium falciparum* malaria in humans. *Cryptosporidium parvum* is a protozoal parasite that infects and destroys cells lining the intestinal tract of humans and animals. The infection establishes quite rapidly and has acute effects on the patient. In the case of humans, patients get severe dysentery for a period of 5-7 days. In immune compromised patients *C. parvum* infections can persist and can be life threatening. In animals *C. parvum* infection is the number one cause of death in young dairy calves. A *C. parvum* infection can be easily diagnosed by symptoms and examination of a stool sample. Once the disease is suspected and/or diagnosed, treatment with a PKG inhibitor can be initiated. The dose would vary between 0.01 mg/kg to 500 mg/kg. Treatments would be one or more time(s) a day, orally or parenterally, until the infection is eliminated. Routinely this dosing period would be 1-3 weeks.

*P. falciparum* causes acute life threatening malarial infections in humans. The infection if left untreated can quite often result in death of the patient. A malaria infection can be easily diagnosed by symptoms and examination of a blood sample from the patient. Treatment would be initiated following diagnosis. A PKG inhibitor would be administered one or more time(s) a day, orally or parenterally, until the infection was eliminated. The dose would range between 0.01 mg/kg to 200 mg/kg.

PKG inhibitors may be administered to a host in need of treatment in a manner similar to that used for other antiprotozoal agents; for example, they may be administered parenterally, orally, topically, or rectally. The dosage to be administered will vary according to the particular compound used, the infectious organism involved, the particular host, the severity of the disease, physical condition of the host, and the selected route of administration; the appropriate dosage can be readily determined by a person skilled in the art. For the treatment of protozoal diseases in human and animals, the dosage may range from 0.01 mg/kg to 500 mg/kg. For prophylactic use in human and animals, the dosage may range from 0.01 mg/kg to 100 mg/kg. For use as an anticoccidial agent, particularly in poultry, the compound is preferably administered in the animals' feed or drinking water. The dosage ranges from 0.1 ppm to 500 ppm.

PKG inhibitors may be formulated according to conventional pharmaceutical compounding techniques. Thus a PKG inhibitor composition may contain, in addition to the active ingredient, a pharmaceutically acceptable carrier and optionally other therapeutic ingredients. The composition may be one that is suitable for oral, rectal, topical, or parenteral (including subcutaneous, intramuscular, and intravenous) administrations, although the most suitable route in any given case will depend on the particular host, and nature and severity of the conditions for which the active ingredient is being administered. The composition may be conveniently presented in unit dosage form and prepared by any of the methods well-known in the art of pharmacy.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

Pharmaceutical compositions of the present invention suitable for parenteral administration may be prepared as solutions or suspensions of these active compounds in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Suitable topical formulations include transdermal devices, aerosols, creams, ointments, lotions, dusting powders, and the like. These formulations may be prepared via conventional methods containing the active ingredient. To illustrate, a cream or ointment is prepared by mixing sufficient quantities of hydrophilic material and water, containing from about 5-10% by weight of the compound, in sufficient quantities to produce a cream or ointment having the desired consistency.

Pharmaceutical compositions suitable for rectal administration wherein the carrier is a solid are most preferably presented as unit dose suppositories. Suitable carriers include cocoa butter and other materials commonly used in the art, and the suppositories may be conveniently formed by admixture of the combination with the softened or melted carrier(s) followed by chilling and shaping moulds.

It should be understood that in addition to the aforementioned carrier ingredients the pharmaceutical formulations described above may include, as appropriate, one or more additional carrier ingredients such as diluents, buffers, flavoring agents, binders, surface-active agents, thickeners, lubricants, preservatives (including anti-oxidants) and the like, and substances included for the purpose of rendering the formulation isotonic with the blood of the intended recipient.

For use in the management of coccidiosis in poultry, a PKG inhibitor may be conveniently administered as a component of a feed composition. Suitable poultry feed composition will typically contain from about 1 ppm to about 1000 ppm, preferably from about 0.01% to about 0.1% percent, by weight of a PKG inhibitor. The optimum levels will naturally vary with the species of Eimeria involved, and can be readily determined by one skilled in the art. Levels of in poultry feed of from about 0.01% to about 0.1% percent by weight of the diet are especially useful in controlling the pathology associated with E. tenella, while the preferred concentration for similar control of intestinal-dwelling species is from about 0.01% to about 0.1% percent by weight of the diet. Amounts of about 0.01% to about 0.1% percent by weight are advantageous in reducing the pathogenic effects of both cecal and intestinal coccidiosis.

In the preparation of poultry feed, a PKG inhibitor may be readily dispersed by mechanically mixing the same in finely ground form with the poultry feedstuff, or with an intermediate formulation (premix) that is subsequently blended with other components to prepare the final poultry feedstuff that is fed to the poultry. Typical components of poultry feedstuffs include molasses, fermentation residues, corn meal, ground and rolled oats, wheat shorts and middlings, alfalfa, clover and meat scraps, together with mineral supplements such as bone meal, calcium carbonate and vitamins.

Compositions containing a compound may also be prepared in powder or liquid concentrate form. In accordance with standard veterinary formulation practice, conventional water soluble excipients, such as lactose or sucrose, may be incorporated in the powders to improve their physical properties. Thus particularly suitable powders of this invention comprise 50 to 100% w/w, and preferably 60 to 80% w/w of the combination and 0 to 50% w/w and preferably 20 to 40% w/w of conventional veterinary excipients. These powders may either be added to animal feedstuffs, for example by way of an intermediate premix, or diluted in animal drinking water.

Liquid concentrates of this invention suitably contain a water-soluble compound combination and may optionally include a veterinarily acceptable water miscible solvent, for example polyethylene glycol, propylene glycol, glycerol, glycerol formal or such a solvent mixed with up to 30% v/v of ethanol. The liquid concentrates may be administered to the drinking water of animals, particularly poultry.

The following examples are provided to illustrate the invention are not to be construed as limiting the scope of the invention in any manner.

EXAMPLE 1

Competitive Binding Assay Using [$^3$H] Inhibitor Compound

PKG is incubated with appropriately diluted [$^3$H] Inhibitor Compound for 60 minutes on ice and free ligand is separated from bound ligand by elution through 0.8 ml G-25 gel filtration columns (purchased from AGTC). The void volume, containing ligand-bound protein, is collected and radioactivity assessed by liquid scintillation counting. For competitive binding studies, excess or appropriately diluted cold competitor(s) are added simultaneously with, or 0.01-5 minutes before, the addition of radiolabeled compound. The concentration of the test compound required to inhibit 50% ($IC_{50}$) of the binding of the labeled inhibitor to the parasite drug binding protein(s) is calculated.

For the competitive binding assay PKG may be the S100 fraction, crude preparation containing PKG activity, or recombinant PKG. Generally, the PKG preparation contains 20-50 μg of protein.

EXAMPLE 2

PKG Catalytic Activity.

E. tenella PKG purified fraction (obtained as described in Example 3) (0.05 μl) is incubated for 2 hours at room temperature in 20 μl of an incubation mixture containing: 25 mM HEPES, pH 7.4, 10 mM $MgCl_2$, 5 mM beta-mercaptoethanol, 20 mM beta-glycerophosphate (or 100 μM sodium orthovanadate), 10 μM cGMP, 2 μM ATP, 10 nM [$^{33}$P] ATP (2000 Ci/mmole), 400 μM Kemptide (or 2 mM Kemptide or 0.43 mg/ml myelin basic protein). The reaction is then quenched with 2.5 μl of 0.25 M phosphoric acid per 20 μl assay volume, and the mixture is spotted on Whatman P81 chromatography paper. The chromatography paper is allowed to dry for 2 minutes, washed 5 times for 3 min. each with 150 mls of 75 mM phosphoric acid, then washed briefly with 95% ethanol. After air drying, labeled kemptide remaining on the filter is quantitated by liquid scintillation counting.

EXAMPLE 3

Purification of the [$^3$H] Inhibitor Compound Binding Protein from E. tenella (a) Preparation of the E. tenella Lysates.

Approximately 6×10$^9$ E. tenella unsporulated oocysts were washed twice in 50 mls of 10 mM Hepes pH 7.4. Oocysts were then suspended in an equal volume of lysis buffer (20% glycerol, 10 mM Hepes, pH 7.4, 0.1 mM sodium orthovanadate, protease inhibitor cocktail, [Sigma P8340, diluted at 1:200]) and an equal volume of 3 mm glass beads and mixed by vortexing at 4° C. for 15 minutes. Oocysts were examined microscopically for breakage; mixing continued until 95% of the oocysts were broken. Glass beads were then removed and washed with 20 mls of lysis buffer which was added to the rest of the suspension. The resulting homogenate was separated from the glass beads and centrifuged at 100,000×g for 1 hr. The pellet was discarded and the supernatant, referred to as the E. tenella S100 fraction, was retained for binding assays and further target purification. After estimating the protein concentration, the S100 fraction was aliquoted and frozen at −80° C.

(b) Purification of an E. tenella [$^3$H]-Inhibitor Compound Binding Protein.

The S100 fraction was dialyzed against 2 L of Buffer A (30 mM sodium phosphate, pH 7.4, 1 mM DTT, 1 mM EDTA, 20% glycerol, 10 mM sodium fluoride, 0.1 mM sodium orthovanadate) overnight at room temperature. The dialysate was centrifuged at 100,000×g for 1 hour and the pellet discarded. The supernatant was applied to a HiLoad Q 26/10 column (Pharmacia) that had been equilibrated in Buffer A. The column was washed with buffer A until the OD at 280 nm had returned to baseline indicating that no further protein was eluting from the column. The proteins were then eluted using a linear sodium chloride gradient (0-1 M NaCl) in Buffer A. Each fraction was tested for binding using [$^3$H] Inhibitor Compound (described in Example 1 above). The binding activity eluted as a single peak and fractions containing binding activity were pooled and dialyzed overnight against 2 L Buffer B (30 mM sodium phosphate, pH 7.4, 1 mM DTT, 1 mM EDTA, 10 mM sodium fluoride, 0.1 mM sodium orthovanadate, 1 M ammonium sulfate). The dialysed pool was applied to a butyl sepharose column (Pharmacia) that had been equilibrated in Buffer B. The column was washed with buffer B until the OD at 280 nm had returned to baseline indicating that no further protein was eluting from the column. The proteins were eluted from the column with a linear inverse gradient of ammonium sulfate (from 1 M to no ammonium sulfate) in Buffer B. Each fraction was tested for [$^3$H] Inhibitor Compound binding as above and the fractions containing binding activity pooled and dialyzed overnight against 2 L Buffer C (10 mM sodium phosphate, pH 7.4, 1 mM DTT, 10 mM sodium fluoride, 0.1 mM sodium orthovanadate). The dialysate was applied to a hydroxyapatite column (Biorad) that had been equilibrated in Buffer C. The column was washed with Buffer C until the OD at 280 nm had returned to baseline indicating that no further protein was eluting from the column. Proteins were eluted from the column using a linear gradient of sodium phosphate (10-400 mM sodium phosphate) in Buffer C. The fractions were tested for binding to [$^3$H] Inhibitor Compound as described in Example 1, and the fractions containing binding activity were pooled and dialyzed overnight against 2 L Buffer A. The dialysate was applied to a MonoQ 5/5 column (Pharmacia) that had been equilibrated in Buffer A, the column was washed with buffer A until the OD at 280 nm had returned to baseline indicating that no further protein was eluting from the column. The proteins were then eluted using a linear gradient of sodium chloride (zero to 1 M) in Buffer A. Each fraction was tested for binding to [$^3$H] Inhibitor Compound as above. Aliquots of the fractions containing binding activity were applied to 4-20% or 4-12% polyacrylamide gels (Novex) and electrophoresis was performed in the presence of SDS. The completed gels were stained with a silver stain kit according to the manufacturers instructions (Daiichi Pure Chemical Co. Ltd.). The two peak binding fractions are referred to as "PKG purified fraction" in subsequent experiments.

In the peak fractions a 120 kDa protein was identified that eluted with the same profile as the [$^3$H] Inhibitor Compound binding activity. This protein was excised from a Coomassie Blue stained polyacrylamide gel, tryptic peptides generated and peptide sequence obtained. The peptides obtained are shown below:

```
1. AENRQFLA              [SEQ ID NO:1]

2. VLYIL                 [SEQ ID NO:2]

3. LVSIK                 [SEQ ID NO:3]

4. EDTQAEDARLLGHLEK      [SEQ ID NO:4]

5. EMPTASTGTPEQQQQQQQQ   [SEQ ID NO:5]

6. HGEEQQQERKPSQQQQN     [SEQ ID NO:6]

7. VFLXIV                [SEQ ID NO:7]
```

EXAMPLE 4

Cloning of the cDNA Encoding the *E. tenella* Inhibitor Compound Binding Protein A series of degenerate oligonucleotides were synthesized from the sequence of the peptides listed above. Combinations of these degenerate oligonucleotides were used in coupled reverse transcriptase-polymerase chain reactions (RT-PCR). RNA prepared from unsporulated oocysts of *E. tenella* was used as substrate with random hexamer primers in a reaction catalyzed by reverse transcriptase to synthesize cDNA copies of the RNA. An aliquot of this cDNA was then used as a template in a series of PCR reactions along with various combinations of the degenerate oligonucleotides described above.

Nested PCR reactions using the primary PCR reaction product as template and a different degenerate oligonucleotide(s) from the initial group of primers described above were performed to better identify interesting cDNA products. Those skilled in the method recognize that promiscuous hybridization of primers can and does occur during PCR reactions and that the frequency of promiscuous hybridization increases enormously when degenerate oligonucleotides are used. By performing a secondary or nested PCR reaction with a different single or pair of degenerate oligonucleotide primers derived from the initial set of peptide sequences, one can have far greater confidence in the authenticity of the PCR reaction product(s) as it relates to the protein of interest. Using this criteria for selection, several of the RT-PCR reaction products were cloned and sequenced in an attempt to identify an internal deduced peptide identical to one of the native peptides and/or an open reading frame (ORF) that bears resemblence to a known sequence in sequence databases. One of the RT-PCR products (clone Et.52035) has a single open reading frame defined at one end by a degenerate oligonucleotide derived from the fourth peptide listed above and at the other end by a degenerate oligonucleotide derived from the first peptide listed above. Moreover, this ORF from clone Et.52035 has limited amino acid sequence identity with a *D. melanogaster* cGMP-dependent protein kinase (PKG) and the regulatory subunit of a *S. cerevisiae* cAMP-dependent protein kinase. The nucleotide sequence of clone Et.52035 is shown as SEQ ID NO: 8, and the deduced amino acid sequence is shown as SEQ ID NO:9. The degenerate oligonucleotides that were used to generate the Et.52035 PCR product are listed below. In the primary PCR reaction, oligonucleotides AG1-2 (from peptide SEQ ID NO:5) and AG4-1 (from SEQ ID NO:1) were used as a primer pair. The product of this PCR was then used as substrate in a secondary reaction with oligonucleotides AG3-1 (from peptide SEQ ID NO:4) and AG4-1 as a primer pair.

```
AG1-2:                                    (SEQ ID NO: 14)
5'-ACN GGN CAN CCN GA(A/G) CA(A/G) CA-3'

AG4-1:                                    (SEQ ID NO: 15)
5'-GCN A(A/G)(A/G) AA(C/T) TGN C(T/G)(A/G) TT(C/T)
TC-3'

AG3-1:                                    (SEQ ID NO: 16)
5'-GA(A/G) GA(C/T) ACN CA(A/G) GCN GA(A/G) GA(C/T)
GC-3'
```

The insert from clone Et.52035 was used as a hybridization probe to screen an *E. tenella* cDNA library. The cDNA library was constructed by methods common in the art. Total RNA was prepared from unsporulated oocysts (USO) of *E. tenella*. Poly (A) RNA was twice selected using oligo (dT) cellulose chromatography and used as a template for first strand cDNA synthesis with SuperScript reverse transcriptase (Life Technologies, Inc.) and primed with oligo (dT). Following second strand cDNA synthesis and EcoR I adapter ligation, double stranded cDNA was size fractionated by column chromatography using Sephacryl S-500 HR and then ligated into the phage vector lambda ZAP II (Stratagene). Ligation reaction products were then packaged using Gigapack III Gold packaging extract (Stratagene) according to the manufacturer's recommendations. A total of $1.25 \times 10^6$ recombinant phage were screened using the 453 base pair insert from clone Et.52035. Several plaque-pure positive clones were isolated from each library and subcloned into pBluescript SK (Stratagene) by in vivo excision according to the manufacturer's recommendations. Phagemid clones were characterized by restriction enzyme mapping and partial nucleotide sequence analysis. Automated DNA sequence was performed using an Applied Biosystems model 373 instrument with the Prism FS cycle sequencing kit.

The longest cDNA clone purified in this screen (Et.PKG7) is nearly 4.3 kb in length with a deduced ORF of 1003 amino acids, capable of coding for a protein of 113 kDa. Each of the seven peptide sequences from the biochemically purified 120 kDa *E. tenella* protein can be located within this ORF. The nucleotide sequence of Et.PKG7 is shown as SEQ ID NO:10, and the deduced amino acid sequence shown as SEQ ID NO:11. The deduced amino acid sequence still most closely resembles the *Drosophila* PKG; 31% identity to the dual cGMP binding domains and 45% identity to the catalytic domain. Unlike all other PKGs in which these two functional domains are close to one another along the length of the protein, the *Eimeria* gene product is predicted to have nearly 300 amino acids between the two domains. This 300 amino acid length accounts for the majority of the size difference between the *Eimeria* protein and other PKGs.

EXAMPLE 5

Cloning of the *T. gondii* cDNA Homologue of *E. tenella* PKG7

A 753 nucleotide length of *E. tenella* cDNA clone PKG7 (nucleotide position 2573 to 3325 within SEQ ID NO:10) was amplified by PCR and used as a probe to screen a *T. gondii* cDNA library using reduced hybridization stringency to isolate a PKG homologue from this related protozoan parasite. This region of the *Eimeria* cDNA clone was chosen because it comprises the majority of the catalytic domain of the deduced protein product and is the region which is most highly conserved evolutionarily among PKG entries in nucleic acid databases. Full length *T. gondii* cDNA clones nearly 4.0 kb in length have been sequenced and code for a deduced protein 994 amino acids in length which is 69% identical and 77% similar to the protein predicted from *E. tenella* clone PKG7. The nucleotide sequence encoding *T. gondii* PKG is shown as SEQ ID NO:12, and the deduced amino acid sequence as SEQ ID NO:13.

EXAMPLE 6

Functional Recombinant Expression of the Protein Coded for by *E. tenella* PKG7

The open reading frame of cDNA clone Et.PKG7 has been modified by PCR to add six histidine residues at the C-terminal end of the protein. This has been accomplished using methods familiar to those skilled in the art. Oligonucleotide primers which hybridize to the ends of the deduced open reading frame from clone Et.PKG7 were synthesized. The 5'-oligonucleotide starts at what is presumed to be the initiator methionine and has been modified to add a Bam HI cloning site. The 3'-oligonucleotide carries sequence that is complementary to the nucleotide sequence that encodes the final six deduced amino acid residues of Et PKG. Following this the synthetic oligonucleotide has 18 nucleotides capable of coding for six consecutive histidine residues. This length in turn is followed by a TAA nucleotide triplet (a translation termination codon) and then a Xba I restriction enzyme recognition sequence for cloning purposes. These two synthetic primers were used in a PCR reaction with Et.PKG7 as template to generate a cDNA that corresponds to the protein coding region and which can be subcloned directionally as a 5'-Bam HI/3'-Xba I fragment into the baculovirus expression vector pFastBac1 (Life Technologies) for recombinant protein expression in invertebrate cells. The hexa-histidine motif serves both as an epitope to follow the expression and purification of the recombinant protein by Western blotting as well as an affinity tag to aid in the purification of recombinant Et.PKG7 by immobilized metal chelate affinity chromatography (IMAC). Western blot positive recombinant protein expressed in invertebrate Sf9 cells has been partially purified by sequential IMAC and cGMP-agarose affinity chromatographies (see below) for biochemical characterization.

EXAMPLE 7

Identification of the Native 120 kDa *E. tenella* [$^3$H] Inhibitor Compound Binding Protein and the Recombinant Protein Expressed from cDNA Clone Et.PKG7 as a cGMP-Dependent Protein Kinase (a) PKG catalytic activity. *E. tenella* PKG purified fraction as described above (0.05 µl) was incubated for 2 hours at room temperature in 20 µl of an incubation mixture containing: 25 mM HEPES, pH 7.4, 10 mM $MgCl_2$, 5 mM beta-mercaptoethanol, 20 mM beta-glycerophosphate (or 100 µM sodium orthovanadate), 10 µM cGMP, 2 µM ATP, 10 nM [$^{33}$P] ATP (2000 Ci/mmole), 400 µM Kemptide (or 2 mM Kemptide or 0.43 mg/ml myelin basic protein). The reaction was then quenched with 2.5 µl of 0.25 M phosphoric acid per 20 µl assay volume, and the mixture was spotted on Whatman P81 chromatography paper. The chromatography paper was allowed to dry for 2 minutes, washed 5 times for 3 min. each with 150 mls of 75 mM phosphoric acid, then washed briefly with 95% ethanol. After air drying, labeled kemptide remaining on the filter was quantitated by liquid scintillation counting.

The biochemically purified native *E. tenella* Inhibitor Compound binding protein contained very little kinase activity when tested in the absence of cyclic nucleotide cofactors. Kinase activity was marginally stimulated when assayed in the presence of cAMP, but was stimulated by greater than 400 fold with cGMP.

(b) "In-gel" kinase assay. To confirm that the kinase activity was contributed by the 120 kDa polypeptide and not by another minor protein in this biochemical fraction, an "in gel" kinase assay was conducted (see method below). The in gel kinase assay was performed according to the manufacturers instructions (Stratagene In-Gel Protein Kinase Assay Kit, Instruction Manual Cat. # 206020, Revision # 117002) except that the substrate provided in the kit was replaced with 0.33 mg myelin basic protein per ml of gel. In this method an SDS-polyacrylamide gel is impregnated with a kinase substrate and the purified fraction is electrophoresed into the gel. Following extensive washing to renature the kinase after exposure to SDS, $^{32}$P ATP and cGMP were added. The label becomes incorporated into the substrate at positions where catalytically active kinases are present. In this assay label was incorporated only at the position of the 120 kDa protein.

(c) Soluble proteins derived from a lysate of *E. tenella* were chromatographed on a HiLoad Q column (see Example 3 above). Fractions were tested for kinase and binding activities. The results indicate that these two activities are coincident, providing further confirmation that the binding to [³H] Inhibitor Compound and kinase activity reside in the same protein.

(d) cGMP agarose affinity chromatography. A 1 ml cGMP agarose column (Biolog) was equilibrated with cGMP agarose buffer (50 mM Hepes, pH 7.4, 10% glycerol, 10 mM sodium fluoride, 0.1 mM sodium orthovanadate, 1 mM EDTA) and the purified fraction applied to the column. The column was washed with 10 ml of cGMP agarose buffer. Non-specifically bound proteins were removed by washing with 5 ml of cGMP agarose buffer containing 1 mM GMP. Proteins were eluted with 5 ml of cGMP agarose buffer containing 15 mM cGMP and fractions were collected. Fractions were analyzed for [³H]-Inhibitor Compound binding, PKG activity and by silver staining following polyacrylamide gel electrophoresis. The affinity matrix, cGMP agarose (Biolog) binds cGMP binding proteins. When the purified native parasite PKG fraction was applied to such a column all of the Inhibitor Compound binding activity and PKG catalytic activity bound to the column and could be eluted with cGMP but not with GMP (see below). Stained gels of the eluates showed that the only protein eluted from the column was the 120 kDa polypeptide. Recombinant protein expressed in invertebrate cells from cDNA clone Et. PKG7 and partially purified by IMAC chromatography also binds to the cGMP-agarose affinity matrix and can be specifically eluted with buffer containing cGMP. Recombinant protein purified by these sequential affinity chromatographies is also a catalytically active PKG.

The results from the above assays demonstrate that the 120 kDa *E. tenella* protein is a PKG and that it specifically binds Inhibitor Compound. In addition, both the native and the recombinant expressed PKG catalytic activity can be inhibited with Inhibitor Compound with an IC50 of <5 nM.

What is claimed is:

1. A substantially pure cGMP dependent protein kinase comprising the amino acid sequence as set forth in SEQ ID NO:13.

2. A method of screening for substances which inhibit the kinase activity of the substantially pure cGMP dependent protein kinase of claim 1, comprising contacting said substantially pure cGMP dependent protein kinase with a substance to be screened and measuring the cGMP dependent protein kinase activity, wherein inhibition of the cGMP dependent protein kinase activity indicates the substance is an inhibitor of the cGMP dependent protein kinase activity of the substantially pure cGMP dependent protein kinase of claim 1.

3. A method for identifying an agent effective at inhibiting the kinase activity of the substantially pure cGMP dependent protein kinase of claim 1, said method comprising the steps of: (i) combining in a reaction mixture (a) a test agent, (b) the substantially pure cGMP dependent protein kinase of claim 1, (c) a suitable substrate for said kinase of (b) above, and (d) labeled ATP; and (ii) determining the extent to which the test agent inhibits phosphorylation of the substrate as compared to a control reaction lacking the test compound, wherein inhibition of phosphorylation of the substrate in the presence of the compound is indicative that the test agent is an agent effective at inhibiting the kinase activity of the substantially pure cGMP dependent protein kinase of claim 1.

4. A method of screening for a compound that inhibits the binding or kinase activity of the substantially pure cGMP dependent protein kinase of claim 1, said method comprising: (a) combining the substantially pure cGMP dependent protein kinase of claim 1 with at least one test compound under conditions permissive for the activity of said kinase; and (b) assessing the binding or kinase activity of said kinase in the presence of the test compound; and (c) comparing the binding or kinase activity of said kinase in the presence of the test compound with the binding or kinase activity of said kinase in the absence of the test compound, wherein a decrease in the binding or kinase activity is indicative of a compound that inhibits the binding or kinase activity of the substantially pure cGMP dependent protein kinase of claim 1.

* * * * *